(12) United States Patent
Wang et al.

(10) Patent No.: US 12,708,352 B2
(45) **Date of Patent: *Aug. 18, 2026**

(54) DEVICE FOR LEFT ATRIAL APPENDAGE

(71) Applicant: BOSTON SCIENTIFIC SCIMED, INC., Maple Grove, MN (US)

(72) Inventors: Jerry Wang, Edina, MN (US); Joshua Mark Inouye, Brooklyn Park, MN (US); James M. Anderson, Corcoran, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 221 days.

This patent is subject to a terminal disclaimer.

(21) Appl. No.: 18/444,927

(22) Filed: Feb. 19, 2024

(65) Prior Publication Data

US 2024/0277325 A1 Aug. 22, 2024

Related U.S. Application Data

(60) Provisional application No. 63/446,928, filed on Feb. 20, 2023.

(51) Int. Cl.
*A61N 1/39* (2006.01)
*A61B 17/00* (2006.01)

(52) U.S. Cl.
CPC .................. *A61B 17/00234* (2013.01); *A61B 2017/00243* (2013.01); *A61B 2017/00876* (2013.01)

(58) Field of Classification Search
CPC .......... A61B 2017/00243; A61B 2017/00876; A61B 17/0643; A61B 17/0644;
(Continued)

(56) References Cited

U.S. PATENT DOCUMENTS

| | | | |
|---|---|---|---|
| 178,283 | A | 6/1876 | French |
| 1,967,318 | A | 7/1934 | Monahan |

(Continued)

FOREIGN PATENT DOCUMENTS

| | | | |
|---|---|---|---|
| CN | 1399571 | A | 2/2003 |
| CN | 202143640 | U | 2/2012 |

(Continued)

OTHER PUBLICATIONS

International Search Report and Written Opinion dated Aug. 3, 2004 for International Application No. PCT/US2004/008109.

(Continued)

*Primary Examiner* — Jon Eric C Morales
(74) *Attorney, Agent, or Firm* — Seager, Tufte & Wickhem LLP

(57) ABSTRACT

Blood stagnation within a left atrial appendage (LAA) may be reduced by creating movement within the LAA. A variety of different actuatable devices, including magnetically actuated devices, may be implanted within the LAA. The actuatable device may be caused to become actuated, thereby causing the motion within the LAA. In some cases, causing the actuatable device to become actuated may include application of a magnetic field. In some cases, causing the actuatable device to become actuated may include subjecting the actuatable device to blood flow within the LAA.

20 Claims, 9 Drawing Sheets

(58) Field of Classification Search

CPC .............. A61B 17/068; A61B 17/0682; A61B 17/12013; A61B 17/12031; A61B 17/12122; A61B 17/12136; A61B 17/1214; A61B 17/12145; A61B 17/12159; A61B 17/12168; A61B 17/12172; A61B 17/122; A61B 2017/00292; A61B 2017/00367; A61B 2017/00477; A61B 2017/00632; A61B 2017/00867; A61B 2017/0641; A61B 2017/0647; A61B 2017/0649; A61B 2017/081; A61B 2017/1205; A61B 2017/12054; A61B 2017/12095; A61B 2017/22042; A61B 17/00234; A61B 17/29; A61B 2017/0011; A61B 34/70; A61B 34/73; A61M 2205/0216; A61M 2205/0266; A61M 60/165; A61M 60/187; A61M 60/216; A61M 60/253; A61M 60/258; A61M 60/289; A61M 60/30; A61M 60/454; A61M 60/492; A61M 60/495; A61M 60/861; A61M 60/873; A61M 60/882; A61N 1/395; Y10T 74/20396

See application file for complete search history.

(56) References Cited

U.S. PATENT DOCUMENTS 3,402,710 A 9/1968 Paleschuck
3,540,431 A 11/1970 Mobin-Uddin
3,557,794 A 1/1971 Van Patten
3,638,652 A 2/1972 Kelley
3,811,449 A 5/1974 Gravlee et al.
3,844,302 A 10/1974 Klein
3,874,388 A 4/1975 King et al.
4,007,743 A 2/1977 Blake
4,108,420 A 8/1978 West et al.
4,175,545 A 11/1979 Termanini
4,309,776 A 1/1982 Berguer
4,341,218 A 7/1982 Ü
4,364,392 A 12/1982 Strother et al.
4,425,908 A 1/1984 Simon
4,545,367 A 10/1985 Tucci
4,585,000 A 4/1986 Hershenson
4,603,693 A 8/1986 Conta et al.
4,611,594 A 9/1986 Grayhack et al.
4,619,246 A 10/1986 Molgaard-Nielsen et al.
4,638,803 A 1/1987 Rand et al.
4,665,906 A 5/1987 Jervis
4,681,588 A 7/1987 Ketharanathan et al.
4,710,192 A 12/1987 Liotta et al.
4,718,417 A 1/1988 Kittrell et al.
4,759,348 A 7/1988 Cawood et al.
4,781,177 A 11/1988 Lebigot
4,793,348 A 12/1988 Palmaz
4,827,907 A 5/1989 Tashiro
4,832,055 A 5/1989 Palestrant
4,873,978 A 10/1989 Ginsburg
4,917,089 A 4/1990 Sideris
4,921,484 A 5/1990 Hillstead
4,960,412 A 10/1990 Fink
4,966,150 A 10/1990 Etienne et al.
4,998,972 A 3/1991 Chin et al.
5,037,810 A 8/1991 Saliba, Jr.
5,041,090 A 8/1991 Scheglov et al.
5,041,093 A 8/1991 Chu
5,042,707 A 8/1991 Taheri
5,053,009 A 10/1991 Herzberg
5,064,435 A 11/1991 Porter
5,071,407 A 12/1991 Termin et al.
5,078,736 A 1/1992 Behl
5,098,440 A 3/1992 Hillstead
5,108,418 A 4/1992 Lefebvre
5,108,420 A 4/1992 Marks
5,108,474 A 4/1992 Riedy et al.
5,116,360 A 5/1992 Pinchuk et al.
5,122,136 A 6/1992 Guglielmi et al.
5,171,259 A 12/1992 Inoue
5,171,383 A 12/1992 Sagaye et al.
5,176,692 A 1/1993 Wilk et al.
5,192,301 A 3/1993 Kamiya et al.
5,211,658 A 5/1993 Clouse
5,234,458 A 8/1993 Metais
5,256,146 A 10/1993 Ensminger et al.
5,258,000 A 11/1993 Gianturco
5,258,042 A 11/1993 Mehta
5,279,539 A 1/1994 Bohan et al.
5,284,488 A 2/1994 Sideris
5,304,184 A 4/1994 Hathaway et al.
5,306,234 A 4/1994 Johnson
5,312,341 A 5/1994 Turi
5,329,942 A 7/1994 Gunther et al.
5,334,217 A 8/1994 Das
5,344,439 A 9/1994 Otten
5,350,398 A 9/1994 Pavcnik et al.
5,350,399 A 9/1994 Erlebacher et al.
5,353,784 A 10/1994 Nady-Mohamed
5,366,460 A 11/1994 Eberbach
5,366,504 A 11/1994 Andersen et al.
5,370,657 A 12/1994 Irie
5,375,612 A 12/1994 Cottenceau et al.
5,397,331 A 3/1995 Himpens et al.
5,397,355 A 3/1995 Marin et al.
5,409,444 A 4/1995 Kensey et al.
5,417,699 A 5/1995 Klein et al.
5,421,832 A 6/1995 Lefebvre
5,425,744 A 6/1995 Fagan et al.
5,427,119 A 6/1995 Swartz et al.
5,433,727 A 7/1995 Sideris
5,443,454 A 8/1995 Tanabe et al.
5,443,478 A 8/1995 Purdy et al.
5,451,235 A 9/1995 Lock et al.
5,454,365 A 10/1995 Bonutti
5,464,408 A 11/1995 Duc
5,469,867 A 11/1995 Schmitt
5,490,856 A 2/1996 Person et al.
5,497,774 A 3/1996 Swartz et al.
5,499,975 A 3/1996 Cope et al.
5,499,995 A 3/1996 Teirstein
5,522,790 A 6/1996 Moll et al.
5,522,822 A 6/1996 Phelps et al.
5,522,836 A 6/1996 Palermo
5,527,322 A 6/1996 Klein et al.
5,527,338 A 6/1996 Purdy
5,558,093 A 9/1996 Pomeranz et al.
5,558,652 A 9/1996 Henke
5,569,204 A 10/1996 Cramer et al.
5,591,196 A 1/1997 Marin et al.
5,614,204 A 3/1997 Cochrum
5,634,936 A 6/1997 Linden et al.
5,634,942 A 6/1997 Chevillon et al.
5,637,097 A 6/1997 Yoon
5,643,282 A 7/1997 Kieturakis
5,643,292 A 7/1997 Hart
5,649,953 A 7/1997 Lefebvre
5,653,690 A 8/1997 Booth et al.
5,662,671 A 9/1997 Barbut et al.
5,669,933 A 9/1997 Simon et al.
5,681,345 A 10/1997 Euteneuer
5,681,347 A 10/1997 Cathcart et al.
5,683,411 A 11/1997 Kavteladze et al.
5,690,671 A 11/1997 McGurk et al.
5,693,067 A 12/1997 Purdy
5,695,525 A 12/1997 Mulhauser et al.
5,700,285 A 12/1997 Myers et al.
5,702,421 A 12/1997 Schneidt
5,704,910 A 1/1998 Humes
5,709,224 A 1/1998 Behl et al.
5,709,704 A 1/1998 Nott et al.
5,709,707 A 1/1998 Lock et al.
5,722,400 A 3/1998 Ockuly et al.
5,724,975 A 3/1998 Negus et al.

(56) References Cited

U.S. PATENT DOCUMENTS 5,725,512 A 3/1998 Swartz et al.
5,725,552 A 3/1998 Kotula et al.
5,725,568 A 3/1998 Hastings
5,733,294 A 3/1998 Forber et al.
5,733,302 A 3/1998 Myler et al.
5,735,290 A 4/1998 Sterman et al.
5,749,880 A 5/1998 Banas et al.
5,749,883 A 5/1998 Halpern
5,749,894 A 5/1998 Engelson
5,766,219 A 6/1998 Horton
5,766,246 A 6/1998 Mulhauser et al.
5,769,816 A 6/1998 Barbut et al.
5,776,097 A 7/1998 Massoud
5,776,162 A 7/1998 Kleshinski
5,782,860 A 7/1998 Epstein et al.
5,785,679 A 7/1998 Abolfathi et al.
5,800,454 A 9/1998 Jacobsen et al.
5,800,457 A 9/1998 Gelbfish
5,800,512 A 9/1998 Letnz et al.
5,807,261 A 9/1998 Benaron et al.
5,810,874 A 9/1998 Lefebvre
5,814,028 A 9/1998 Swartz et al.
5,814,029 A 9/1998 Hassett
5,814,064 A 9/1998 Daniel
5,820,591 A 10/1998 Thompson et al.
5,823,198 A 10/1998 Jones et al.
5,830,228 A 11/1998 Knapp et al.
5,833,673 A 11/1998 Ockuly et al.
5,836,913 A 11/1998 Orth et al.
5,836,968 A 11/1998 Simon et al.
5,840,027 A 11/1998 Swartz et al.
5,843,118 A 12/1998 Sepetka et al.
5,846,260 A 12/1998 Maahs
5,846,261 A 12/1998 Kotula et al.
5,848,969 A 12/1998 Panescu et al.
5,849,005 A 12/1998 Garrison et al.
5,851,232 A 12/1998 Lois
5,853,422 A 12/1998 Huebsch et al.
5,855,597 A 1/1999 Jayaraman
5,865,791 A 2/1999 Whayne et al.
5,865,802 A 2/1999 Yoon et al.
5,868,702 A 2/1999 Stevens et al.
5,868,708 A 2/1999 Hart et al.
5,876,367 A 3/1999 Kaganov et al.
5,879,296 A 3/1999 Ockuly et al.
5,879,366 A 3/1999 Shaw et al.
5,882,340 A 3/1999 Yoon
5,885,258 A 3/1999 Sachdeva et al.
5,891,558 A 4/1999 Bell et al.
5,895,399 A 4/1999 Barbut et al.
5,902,289 A 5/1999 Swartz et al.
5,904,680 A 5/1999 Kordis et al.
5,904,703 A 5/1999 Gilson
5,906,207 A 5/1999 Shen
5,910,154 A 6/1999 Tsugita et al.
5,911,734 A 6/1999 Tsugita et al.
5,916,236 A 6/1999 Muijs Van de Moer et al.
5,925,060 A 7/1999 Forber
5,925,063 A 7/1999 Khosravi
5,925,074 A 7/1999 Gingras et al.
5,925,075 A 7/1999 Myers et al.
5,928,192 A 7/1999 Maahs
5,928,260 A 7/1999 Chin et al.
5,931,818 A 8/1999 Werp et al.
5,935,145 A 8/1999 Villar et al.
5,935,147 A 8/1999 Kensey et al.
5,935,148 A 8/1999 Villar et al.
5,941,249 A 8/1999 Maynard
5,941,896 A 8/1999 Kerr
5,944,738 A 8/1999 Amplatz et al.
5,947,997 A 9/1999 Pavcnik et al.
5,951,589 A 9/1999 Epstein et al.
5,951,599 A 9/1999 McCrory
5,954,694 A 9/1999 Sunseri
5,954,767 A 9/1999 Pajotin et al.
5,957,940 A 9/1999 Tanner et al.
5,961,545 A 10/1999 Lentz et al.
5,976,174 A 11/1999 Ruiz
5,980,514 A 11/1999 Kupiecki et al.
5,980,555 A 11/1999 Barbut et al.
5,989,281 A 11/1999 Barbut et al.
5,993,469 A 11/1999 McKenzie et al.
5,993,483 A 11/1999 Gianotti
5,997,557 A 12/1999 Barbut et al.
6,004,280 A 12/1999 Buck et al.
6,004,348 A 12/1999 Banas et al.
6,007,523 A 12/1999 Mangosong
6,007,557 A 12/1999 Ambrisco et al.
6,010,517 A 1/2000 Baccaro
6,010,522 A 1/2000 Barbut et al.
6,013,093 A 1/2000 Nott et al.
6,024,751 A 2/2000 Lovato et al.
6,024,754 A 2/2000 Engelson
6,024,755 A 2/2000 Addis
6,024,756 A 2/2000 Huebsch et al.
6,027,520 A 2/2000 Tsugita et al.
6,033,420 A 3/2000 Hahnen
6,036,720 A 3/2000 Abrams et al.
6,042,598 A 3/2000 Tsugita et al.
6,048,331 A 4/2000 Tsugita et al.
6,051,014 A 4/2000 Jang
6,051,015 A 4/2000 Maahs
6,056,720 A 5/2000 Morse
6,063,070 A 5/2000 Eder
6,063,113 A 5/2000 Kavteladze et al.
6,066,126 A 5/2000 Li et al.
6,068,621 A 5/2000 Balceta et al.
6,074,357 A 6/2000 Kaganov et al.
6,076,012 A 6/2000 Swanson et al.
6,079,414 A 6/2000 Roth
6,080,182 A 6/2000 Shaw et al.
6,080,183 A 6/2000 Tsugita et al.
6,083,239 A 7/2000 Addis
6,090,084 A 7/2000 Hassett et al.
6,096,052 A 8/2000 Callister et al.
6,096,053 A 8/2000 Bates et al.
6,110,243 A 8/2000 Wnenchak et al.
6,123,715 A 9/2000 Amplatz
6,124,523 A 9/2000 Banas et al.
6,132,438 A 10/2000 Fleischman et al.
6,135,991 A 10/2000 Muni et al.
6,136,016 A 10/2000 Barbut et al.
6,139,527 A 10/2000 Laufer et al.
6,139,573 A 10/2000 Sogard et al.
6,152,144 A 11/2000 Lesh et al.
6,152,946 A 11/2000 Broome et al.
6,156,055 A 12/2000 Ravenscroft
6,159,195 A 12/2000 Ha et al.
6,161,543 A 12/2000 Cox et al.
6,168,615 B1 1/2001 Ken et al.
6,171,329 B1 1/2001 Shaw et al.
6,179,859 B1 1/2001 Bates et al.
6,193,739 B1 2/2001 Chevillon et al.
6,203,531 B1 3/2001 Ockuly et al.
6,206,907 B1 3/2001 Marino et al.
6,214,029 B1 4/2001 Thill et al.
6,221,092 B1 4/2001 Koike et al.
6,231,561 B1 5/2001 Frazier et al.
6,231,589 B1 5/2001 Wessman et al.
6,235,045 B1 5/2001 Barbut et al.
6,245,012 B1 6/2001 Kleshinski
6,251,122 B1 6/2001 Tsukernik
6,258,115 B1 7/2001 Dubrul
6,267,772 B1 7/2001 Mulhauser et al.
6,267,776 B1 7/2001 O'Connell
6,270,490 B1 8/2001 Hahnen
6,270,530 B1 8/2001 Eldridge et al.
6,270,902 B1 8/2001 Tedeschi et al.
6,277,138 B1 8/2001 Levinson et al.
6,285,898 B1 9/2001 Ben-Haim
6,290,674 B1 9/2001 Roue et al.
6,290,708 B1 9/2001 Kugel et al.
6,312,407 B1 11/2001 Zadno-Azizi et al.
6,319,251 B1 11/2001 Tu et al.

(56) References Cited

U.S. PATENT DOCUMENTS 6,328,727 B1 12/2001 Frazier et al.
6,328,755 B1 12/2001 Marshall
6,342,062 B1 1/2002 Suon et al.
6,346,116 B1 2/2002 Brooks et al.
6,346,895 B1 2/2002 Lee et al.
6,361,545 B1 3/2002 Macoviak et al.
6,364,895 B1 4/2002 Greenhalgh
6,368,338 B1 4/2002 Kónya et al.
6,371,971 B1 4/2002 Tsugita et al.
6,375,670 B1 4/2002 Greenhalgh
6,391,044 B1 5/2002 Yadav et al.
6,398,803 B1 6/2002 Layne et al.
6,402,746 B1 6/2002 Whayne et al.
6,402,771 B1 6/2002 Palmer et al.
6,402,779 B1 6/2002 Colone et al.
6,419,669 B1 7/2002 Frazier et al.
6,440,152 B1 8/2002 Gainor et al.
6,443,972 B1 9/2002 Bosma et al.
6,447,530 B1 9/2002 Ostrovsky et al.
6,454,775 B1 9/2002 Demarais et al.
6,458,145 B1 10/2002 Ravenscroft et al.
6,464,712 B1 10/2002 Epstein et al.
6,468,291 B2 10/2002 Bates et al.
6,468,301 B1 10/2002 Amplatz et al.
6,485,501 B1 11/2002 Green
6,488,689 B1 12/2002 Kaplan et al.
6,511,496 B1 1/2003 Huter et al.
6,514,280 B1 2/2003 Gilson
6,517,573 B1 2/2003 Pollock et al.
6,533,782 B2 3/2003 Howell et al.
6,547,760 B1 4/2003 Samson et al.
6,547,815 B2 4/2003 Myers
6,551,303 B1 4/2003 Van Tassel et al.
6,551,344 B2 4/2003 Thill
6,558,401 B1 5/2003 Azizi
6,558,405 B1 5/2003 McInnes
6,558,414 B2 5/2003 Layne
6,562,058 B2 5/2003 Seguin et al.
6,569,184 B2 5/2003 Huter
6,569,214 B2 5/2003 Williams et al.
6,589,214 B2 7/2003 McGuckin et al.
6,589,251 B2 7/2003 Yee et al.
6,599,308 B2 7/2003 Amplatz
6,602,271 B2 8/2003 Adams et al.
6,623,508 B2 9/2003 Shaw et al.
6,641,564 B1 11/2003 Kraus
6,650,923 B1 11/2003 Lesh et al.
6,652,555 B1 11/2003 VanTassel et al.
6,652,556 B1 11/2003 VanTassel et al.
6,666,861 B1 12/2003 Grabek
6,689,150 B1 2/2004 Vantassel et al.
6,699,260 B2 3/2004 Dubrul et al.
6,699,276 B2 3/2004 Sogard et al.
6,702,825 B2 3/2004 Frazier et al.
6,712,836 B1 3/2004 Berg et al.
6,726,701 B2 4/2004 Gilson et al.
6,730,108 B2 5/2004 Van Tassel et al.
6,755,812 B2 6/2004 Peterson et al.
6,827,737 B2 12/2004 Hill et al.
6,837,901 B2 1/2005 Rabkin et al.
6,855,153 B2 2/2005 Saadat
6,911,037 B2 6/2005 Gainor et al.
6,932,838 B2 8/2005 Schwartz et al.
6,942,653 B2 9/2005 Quinn
6,949,113 B2 9/2005 Van Tassel et al.
6,958,061 B2 10/2005 Truckai et al.
6,994,092 B2 2/2006 van der Burg et al.
7,011,671 B2 3/2006 Welch
7,014,645 B2 3/2006 Greene, Jr. et al.
7,037,321 B2 5/2006 Sachdeva et al.
7,044,134 B2 5/2006 Khairkhahan et al.
7,097,651 B2 8/2006 Harrison et al.
7,128,073 B1 10/2006 van der Burg et al.
7,152,605 B2 12/2006 Khairkhahan et al.
7,169,164 B2 1/2007 Borillo et al.
7,179,275 B2 2/2007 McGuckin, Jr. et al.
7,226,466 B2 6/2007 Opolski
7,303,526 B2 12/2007 Sharkey et al.
7,323,002 B2 1/2008 Johnson et al.
7,597,704 B2 10/2009 Frazier et al.
7,678,123 B2 3/2010 Chanduszko
7,695,425 B2 4/2010 Schweich et al.
7,713,282 B2 5/2010 Frazier et al.
7,722,641 B2 5/2010 van der Burg et al.
7,727,189 B2 6/2010 VanTassel et al.
7,735,493 B2 6/2010 van der Burg et al.
7,780,694 B2 8/2010 Palmer et al.
7,799,049 B2 9/2010 Ostrovsky et al.
7,811,300 B2 10/2010 Feller, III et al.
7,811,314 B2 10/2010 Fierens et al.
7,862,500 B2 1/2011 Khairkhahan et al.
7,927,365 B2 4/2011 Fierens et al.
7,972,359 B2 7/2011 Kreidler
8,025,495 B2 9/2011 Hardert et al.
8,043,329 B2 10/2011 Khairkhahan et al.
8,052,715 B2 11/2011 Quinn et al.
8,062,282 B2 11/2011 Kolb
8,080,032 B2 12/2011 van der Burg et al.
8,097,015 B2 1/2012 Devellian
8,221,384 B2 7/2012 Frazier et al.
8,221,445 B2 7/2012 van Tassel et al.
8,287,563 B2 10/2012 Khairkhahan et al.
8,323,309 B2 12/2012 Khairkhahan et al.
8,388,672 B2 3/2013 Khairkhahan et al.
8,491,623 B2 7/2013 Vogel et al.
8,523,897 B2 9/2013 van der Burg et al.
8,535,343 B2 9/2013 van der Burg et al.
8,562,509 B2 10/2013 Bates
8,663,273 B2 3/2014 Khairkhahan et al.
8,685,055 B2 4/2014 VanTassel et al.
8,834,519 B2 9/2014 van der Burg et al.
8,845,711 B2 9/2014 Miles et al.
9,034,006 B2 5/2015 Quinn et al.
9,132,000 B2 9/2015 VanTassel et al.
9,168,043 B2 10/2015 van der Burg et al.
9,211,124 B2 12/2015 Campbell et al.
9,445,895 B2 9/2016 Kreidler
9,554,806 B2 1/2017 Larsen et al.
9,561,037 B2 2/2017 Fogarty et al.
9,561,097 B1 2/2017 Kim et al.
9,629,636 B2 4/2017 Fogarty et al.
9,730,701 B2 8/2017 Tischler et al.
9,883,936 B2 2/2018 Sutton et al.
9,913,652 B2 3/2018 Bridgeman et al.
9,943,299 B2 4/2018 Khairkhahan et al.
9,943,315 B2 4/2018 Kaplan et al.
10,071,181 B1 9/2018 Penegor et al.
10,076,335 B2 9/2018 Zaver et al.
10,143,458 B2 12/2018 Kreidler
2001/0000797 A1 5/2001 Mazzocchi
2001/0020181 A1 9/2001 Layne
2001/0034537 A1 10/2001 Shaw et al.
2001/0037141 A1 11/2001 Yee et al.
2002/0022860 A1 2/2002 Borillo et al.
2002/0035374 A1 3/2002 Borillo et al.
2002/0045931 A1 4/2002 Sogard et al.
2002/0062133 A1 5/2002 Gilson et al.
2002/0082638 A1 6/2002 Porter et al.
2002/0082675 A1 6/2002 Myers
2002/0099439 A1 7/2002 Schwartz et al.
2002/0111647 A1 8/2002 Khairkhahan et al.
2002/0138094 A1 9/2002 Borillo et al.
2002/0138097 A1 9/2002 Ostrovsky et al.
2002/0169475 A1 11/2002 Gainor et al.
2002/0177855 A1 11/2002 Greene, Jr. et al.
2003/0017775 A1 1/2003 Dong et al.
2003/0023262 A1 1/2003 Welch
2003/0023266 A1 1/2003 Borillo et al.
2003/0057156 A1 3/2003 Peterson et al.
2003/0060871 A1 3/2003 Hill et al.
2003/0120337 A1 6/2003 Van Tassel et al.
2003/0181942 A1 9/2003 Sutton et al.
2003/0191526 A1 10/2003 Van Tassel et al.
2003/0195555 A1 10/2003 Khairkhahan et al.

(56) References Cited

U.S. PATENT DOCUMENTS

| | | | |
|---|---|---|---|
| 2003/0204203 | A1 | 10/2003 | Khairkhahan et al. |
| 2003/0208214 | A1 | 11/2003 | Loshakove et al. |
| 2003/0220667 | A1 | 11/2003 | van der Burg et al. |
| 2004/0034366 | A1 | 2/2004 | van der Burg et al. |
| 2004/0049210 | A1 | 3/2004 | VanTassel et al. |
| 2004/0093012 | A1 | 5/2004 | Cully et al. |
| 2004/0098031 | A1 | 5/2004 | van der Burg et al. |
| 2004/0122467 | A1 | 6/2004 | VanTassel et al. |
| 2004/0127935 | A1 | 7/2004 | VanTassel et al. |
| 2004/0158274 | A1 | 8/2004 | WasDyke |
| 2004/0186486 | A1 | 9/2004 | Roue et al. |
| 2004/0215230 | A1 | 10/2004 | Frazier et al. |
| 2004/0220610 | A1 | 11/2004 | Kreidler et al. |
| 2004/0220682 | A1 | 11/2004 | Levine et al. |
| 2004/0230222 | A1 | 11/2004 | van der Burg et al. |
| 2005/0004652 | A1 | 1/2005 | van der Burg et al. |
| 2005/0015109 | A1 | 1/2005 | Lichtenstein |
| 2005/0038470 | A1 | 2/2005 | van der Burg et al. |
| 2005/0049573 | A1 | 3/2005 | Van Tassel et al. |
| 2005/0070952 | A1 | 3/2005 | Devellian |
| 2005/0113861 | A1 | 5/2005 | Corcoran et al. |
| 2005/0125020 | A1 | 6/2005 | Meade et al. |
| 2005/0177182 | A1 | 8/2005 | van der Burg et al. |
| 2005/0203568 | A1 | 9/2005 | Burg et al. |
| 2005/0283186 | A1 | 12/2005 | Berrada et al. |
| 2005/0288704 | A1 | 12/2005 | Cartier et al. |
| 2006/0015136 | A1 | 1/2006 | Besselink |
| 2006/0030877 | A1 | 2/2006 | Martinez et al. |
| 2006/0052816 | A1 | 3/2006 | Bates et al. |
| 2006/0100658 | A1 | 5/2006 | Obana et al. |
| 2006/0155323 | A1 | 7/2006 | Porter et al. |
| 2007/0066993 | A1 | 3/2007 | Kreidler |
| 2007/0083227 | A1 | 4/2007 | van der Burg et al. |
| 2007/0083230 | A1 | 4/2007 | Javois |
| 2007/0150041 | A1 | 6/2007 | Evans et al. |
| 2007/0156123 | A1 | 7/2007 | Moll et al. |
| 2007/0162048 | A1 | 7/2007 | Quinn et al. |
| 2007/0185471 | A1 | 8/2007 | Johnson |
| 2008/0275536 | A1 | 11/2008 | Zarins et al. |
| 2009/0005803 | A1 | 1/2009 | Batiste |
| 2009/0062841 | A1 | 3/2009 | Amplatz et al. |
| 2009/0099647 | A1 | 4/2009 | Glimsdale et al. |
| 2009/0105747 | A1 | 4/2009 | Chanduszko et al. |
| 2009/0112249 | A1 | 4/2009 | Miles et al. |
| 2009/0254195 | A1 | 10/2009 | Khairkhan et al. |
| 2009/0318948 | A1 | 12/2009 | Linder et al. |
| 2010/0004726 | A1 | 1/2010 | Hancock et al. |
| 2010/0049238 | A1 | 2/2010 | Simpson |
| 2010/0106178 | A1 | 4/2010 | Obermiller et al. |
| 2010/0324585 | A1 | 12/2010 | Miles et al. |
| 2011/0054515 | A1 | 3/2011 | Bridgeman et al. |
| 2011/0082495 | A1 | 4/2011 | Ruiz |
| 2011/0098525 | A1 | 4/2011 | Kermode et al. |
| 2011/0218566 | A1 | 9/2011 | van der Burg et al. |
| 2011/0301630 | A1 | 12/2011 | Hendriksen et al. |
| 2012/0029553 | A1 | 2/2012 | Quinn et al. |
| 2012/0035643 | A1 | 2/2012 | Khairkhahan et al. |
| 2012/0065662 | A1 | 3/2012 | van der Burg et al. |
| 2012/0125619 | A1 | 5/2012 | Wood et al. |
| 2012/0172654 | A1 | 7/2012 | Bates |
| 2012/0172927 | A1 | 7/2012 | Campbell et al. |
| 2012/0239077 | A1 | 9/2012 | Zaver et al. |
| 2012/0239083 | A1 | 9/2012 | Kreidler |
| 2012/0245619 | A1 | 9/2012 | Guest |
| 2012/0283585 | A1 | 11/2012 | Werneth et al. |
| 2012/0283773 | A1 | 11/2012 | Van Tassel et al. |
| 2012/0323267 | A1 | 12/2012 | Ren |
| 2013/0006343 | A1 | 1/2013 | Kassab et al. |
| 2013/0012982 | A1 | 1/2013 | Khairkhahan et al. |
| 2013/0018413 | A1 | 1/2013 | Oral et al. |
| 2013/0110154 | A1 | 5/2013 | van der Burg et al. |
| 2013/0165735 | A1 | 6/2013 | Khairkhahan et al. |
| 2013/0211492 | A1 | 8/2013 | Schneider et al. |
| 2013/0331884 | A1 | 12/2013 | Van der Burg et al. |
| 2014/0018841 | A1 | 1/2014 | Peiffer et al. |
| 2014/0039536 | A1 | 2/2014 | Cully et al. |
| 2014/0046360 | A1 | 2/2014 | Van der Burg et al. |
| 2014/0081314 | A1 | 3/2014 | Zaver et al. |
| 2014/0100596 | A1 | 4/2014 | Rudman et al. |
| 2014/0142612 | A1 | 5/2014 | Li et al. |
| 2014/0148842 | A1 | 5/2014 | Khairkhahan et al. |
| 2014/0163605 | A1 | 6/2014 | VanTassel et al. |
| 2014/0188157 | A1 | 7/2014 | Clark |
| 2014/0303719 | A1 | 10/2014 | Cox et al. |
| 2014/0336612 | A1 | 11/2014 | Frydlewski et al. |
| 2014/0336699 | A1 | 11/2014 | van der Burg et al. |
| 2015/0005810 | A1 | 1/2015 | Center et al. |
| 2015/0039021 | A1 | 2/2015 | Khairkhahan et al. |
| 2015/0080903 | A1 | 3/2015 | Dillard et al. |
| 2015/0196300 | A1 | 7/2015 | Tischler et al. |
| 2015/0230909 | A1 | 8/2015 | Zaver et al. |
| 2015/0238197 | A1 | 8/2015 | Quinn et al. |
| 2015/0305727 | A1 | 10/2015 | Karimov et al. |
| 2015/0313604 | A1 | 11/2015 | Roue et al. |
| 2015/0313605 | A1 | 11/2015 | Griffin |
| 2015/0327979 | A1 | 11/2015 | Quinn et al. |
| 2015/0374491 | A1 | 12/2015 | Kreidler |
| 2016/0051358 | A1 | 2/2016 | Sutton et al. |
| 2016/0058539 | A1 | 3/2016 | VanTassel et al. |
| 2016/0066922 | A1 | 3/2016 | Bridgeman et al. |
| 2016/0106437 | A1 | 4/2016 | van der Burg et al. |
| 2016/0192942 | A1 | 7/2016 | Strauss et al. |
| 2016/0287259 | A1 | 10/2016 | Hanson et al. |
| 2016/0331382 | A1 | 11/2016 | Center et al. |
| 2016/0374657 | A1 | 12/2016 | Kreidler |
| 2017/0027552 | A1 | 2/2017 | Turkington et al. |
| 2017/0042550 | A1 | 2/2017 | Chakraborty et al. |
| 2017/0056166 | A1 | 3/2017 | Ratz et al. |
| 2017/0100112 | A1 | 4/2017 | van der Burg et al. |
| 2017/0181751 | A1 | 6/2017 | Larsen et al. |
| 2017/0340336 | A1 | 11/2017 | Osypka |
| 2018/0064446 | A1 | 3/2018 | Figulla et al. |
| 2018/0070950 | A1 | 3/2018 | Zaver et al. |
| 2018/0140412 | A1 | 5/2018 | Sutton et al. |
| 2018/0140413 | A1 | 5/2018 | Quinn et al. |
| 2018/0250014 | A1 | 9/2018 | Melanson et al. |
| 2019/0223883 | A1 | 7/2019 | Anderson et al. |
| 2024/0278028 | A1* | 8/2024 | Wang .................. A61M 60/258 |

FOREIGN PATENT DOCUMENTS

| | | | |
|---|---|---|---|
| CN | 106859722 | A | 6/2017 |
| DE | 10201004476 | A1 | 3/2012 |
| EP | 1523957 | A2 | 4/2005 |
| EP | 1595504 | A1 | 11/2005 |
| EP | 2074953 | A1 | 1/2009 |
| EP | 2481381 | A1 | 8/2012 |
| EP | 2928420 | A1 | 10/2015 |
| EP | 3072461 | A1 | 9/2016 |
| EP | 3372173 | A2 | 9/2018 |
| JP | 2003532457 | A | 11/2003 |
| JP | 2005324019 | A | 11/2005 |
| JP | 2007513684 | A | 5/2007 |
| JP | 2009160402 | A | 7/2009 |
| JP | 2012501793 | A | 1/2012 |
| WO | 9313712 | A1 | 7/1993 |
| WO | 9504132 | A1 | 2/1995 |
| WO | 9522359 | A1 | 8/1995 |
| WO | 9601591 | A1 | 1/1996 |
| WO | 9640356 | A1 | 12/1996 |
| WO | 9721402 | A1 | 6/1997 |
| WO | 9726939 | A1 | 7/1997 |
| WO | 9728749 | A1 | 8/1997 |
| WO | 9735522 | A1 | 10/1997 |
| WO | 9802100 | A1 | 1/1998 |
| WO | 9817187 | A1 | 4/1998 |
| WO | 9822026 | A1 | 5/1998 |
| WO | 9823322 | A1 | 6/1998 |
| WO | 9827868 | A1 | 7/1998 |
| WO | 9905977 | A1 | 2/1999 |
| WO | 9907289 | A1 | 2/1999 |
| WO | 9908607 | A1 | 2/1999 |
| WO | 9923976 | A1 | 5/1999 |
| WO | 9925252 | A1 | 5/1999 |

(56) References Cited

FOREIGN PATENT DOCUMENTS

| | | | |
|---|---|---|---|
| WO | 9930640 | A1 | 6/1999 |
| WO | 9944510 | A1 | 9/1999 |
| WO | 9959479 | A1 | 11/1999 |
| WO | 0001308 | A1 | 1/2000 |
| WO | 0016705 | A1 | 3/2000 |
| WO | 0027292 | A1 | 5/2000 |
| WO | 0035352 | A1 | 6/2000 |
| WO | 0053120 | A1 | 9/2000 |
| WO | 0067669 | A1 | 11/2000 |
| WO | 0108743 | A1 | 2/2001 |
| WO | 0115629 | A1 | 3/2001 |
| WO | 0121247 | A1 | 3/2001 |
| WO | 0126726 | A1 | 4/2001 |
| WO | 0130266 | A1 | 5/2001 |
| WO | 0130267 | A1 | 5/2001 |
| WO | 0130268 | A1 | 5/2001 |
| WO | 0170119 | A1 | 9/2001 |
| WO | 0215793 | A2 | 2/2002 |
| WO | 0224106 | A2 | 3/2002 |
| WO | 02071977 | A2 | 9/2002 |
| WO | 03007825 | A1 | 1/2003 |
| WO | 03008030 | A2 | 1/2003 |
| WO | 03032818 | A1 | 4/2003 |
| WO | 2004012629 | A1 | 2/2004 |
| WO | 2007044536 | A1 | 4/2007 |
| WO | 2010024801 | A1 | 3/2010 |
| WO | 2010081033 | A1 | 7/2010 |
| WO | 2013060855 | A1 | 5/2013 |
| WO | 2013159065 | A1 | 10/2013 |
| WO | 2014011865 | A1 | 1/2014 |
| WO | 2014018907 | A1 | 1/2014 |
| WO | 2014089129 | A1 | 6/2014 |
| WO | 2014106239 | A1 | 7/2014 |
| WO | 2015164836 | A1 | 10/2015 |
| WO | 2016087145 | A1 | 6/2016 |
| WO | 2018017935 | A1 | 1/2018 |
| WO | 2018187732 | A1 | 10/2018 |
| WO | 2019084358 | A1 | 5/2019 |

OTHER PUBLICATIONS

International Search Report and Written Opinion dated Feb. 15, 2000 for International Application No. PCT/US99/26325.
International Search Report dated May 20, 2003 for International Application No. PCT/US02/33808.
Written Opinion dated Nov. 17, 2003 for International Application No. PCT/US/02/33808.
International Search Report and Written Opinion dated Aug. 21, 2018 for International Application No. PCT/US2018/029684.
Cragg et al., "A New Percutaneous Vena Cava Filter," American Journal of Radiology, Sep. 1983, pp. 601-604, vol. 141.
Cragg et al., "Nonsurgical Placement of Arterial Endoprostheses: A New Technique Using Nitinol Wire," Radiology, Apr. 1983, pp. 261-263, vol. 147, No. 1.
Lock et al., "Transcatheter Closure of Atrial Septal Defects." Circulation, May 1989, pp. 1091-1099, vol. 79, No. 5.
Lock et al., "Transcatheter Umbrella Closure of Congenital Heart Defects," Circulation, Mar. 1987, pp. 593-599, vol. 75, No. 3.
Rashkind et al., "Nonsurgical closure of patent ductus arteriosus: clinical application of the Rashkind PDA Occluder System," Circulation, Mar. 1987, pp. 583-592, vol. 75, No. 3.
Rosengart et al., "Percutaneous and Minimally Invasive Valve Procedures," Circulation, Apr. 1, 2008, pp. 1750-1767, vol. 117.
Ruttenberg, "Nonsurgical Therapy of Cardiac Disorders," Pediatric Consult, 1986, Pages not numbered, vol. 5, No. 2.
Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.
Wessel et al., "Outpatient Closure of the Patent Ductus Arteriousus," Circulation, 1988, pp. 1068-1071, vol. 77, No. 5.
Tung et al., U.S. Appl. No. 61/559,941, filed Nov. 15, 2011.
Yue Yu et al., U.S. Appl. No. 61/557,880, filed Dec. 20, 2011.
Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.
International Search Report and Written Opinion dated Apr. 22, 2014 for International Application No. PCT/US2013/078454.
Aryana et al., "Incomplete Closure of the Left Atrial Appendage: Implication and Management." Curr Cardiol Rep., 18(9):82, 2016.
Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.
University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.
Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.
Romero et al., "Left Atrial Appendage Closure Devices," Clinical Medicine Insights: Cardiology, vol. 8, pp. 45-52, 2014.
Invitation To Pay Additional Fees And, Where Applicable, Protest Fee, for International Application No. PCT/US2016/043363, mailed Oct. 13, 2016.
International Search Report and Written Opinion dated Oct. 14, 2019 for International Application No. PCT/US2019/047452.
International Search Report and Written Opinion dated Oct. 27, 2017 for International Application No. PCT/US2017/048150.
International Search Report and Written Opinion dated Jan. 21, 2019 for International Application No. PCT/US2018/051953.
International Search Report and Written Opinion dated Oct. 13, 2016 for International Application No. PCT/US2016/043363.
International Search Report and Written Opinion dated Mar. 17, 20, for International Application No. PCT/US2019/065243.
International Search Report and Written Opinion dated Sep. 9, 2019 for International Application No. PCT/US2019/033698.
Blackshear et al; "Appendage Obliteration to Reduce Stroke in Cardiac Surgical Patients with Atrial Fibrillation", Ann. Thoracic Surgery, pp. 755-759, 1996.
Lindsay, "Obliteration of the Left Atrial Appendage: A Concept Worth Testing", Ann. Thoracic Surgery, 1996.
Invitation To Pay Additional Fees dated Feb. 22, 2019 for International Application No. PCT/US2018/066163.
International Search Report and Written Opinion dated Oct. 23, 2020 for International Application No. PCT/US2020/042192.
Bollman et al., "Frequency Analysis of Human Atrial Fibrillation Using the surface Electrocardiogram and its Response to Ibutilide," The American Journal of Cardiology, vol. 81, Issue 12, pp. 1439-1445, Jun. 15, 1998. (Abstract).

* cited by examiner

DEVICE FOR LEFT ATRIAL APPENDAGE

CROSS-REFERENCE TO RELATED APPLICATIONS

This application claims the benefit of U.S. Provisional Patent Application Ser. No. 63/446,928, filed Feb. 20, 2023, which is incorporated herein by reference.

TECHNICAL FIELD

The disclosure relates generally to medical devices and more particularly to medical devices that are adapted for preventing blood stagnation within a left atrial appendage.

BACKGROUND

The left atrial appendage is a small organ attached to the left atrium of the heart. During normal heart function, as the left atrium constricts and forces blood into the left ventricle, the left atrial appendage constricts and forces blood into the left atrium. The ability of the left atrial appendage to contract assists with improved filling of the left ventricle, thereby playing a role in maintaining cardiac output. However, in patients suffering from atrial fibrillation, the left atrial appendage may not properly contract or empty, causing stagnant blood to pool within its interior, which can lead to the undesirable formation of thrombi within the left atrial appendage.

Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation originate in the left atrial appendage. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example may be found in a method for reducing blood stagnation within a left atrial appendage (LAA) using a magnetic field to cause motion within the LAA. The method includes implanting a magnetically actuated device within the LAA and causing the magnetically actuated device to become actuated, the magnetically actuated device causing motion within the LAA.

Alternatively or additionally, causing the magnetically actuated device to become actuated may include applying an external magnetic field to the magnetically actuated device.

Alternatively or additionally, the magnetically actuated device may include a magnetically actuated component, an anchor adapted to anchor the magnetically actuated component to an interior of the LAA, and a flexible tether extending between the magnetically actuated component and the anchor.

Alternatively or additionally, the magnetically actuated component may include a magnet or a magnetic material.

Alternatively or additionally, causing the magnetically actuated device to become actuated may include subjecting the magnetically actuated device to blood flow within the LAA.

Alternatively or additionally, the magnetically actuated device may include a tapered housing adapted to fit within the LAA and to allow blood flow within the tapered housing. The tapered housing includes a first polarity magnet disposed within a proximal end of the tapered housing and a second polarity magnet disposed within a distal end of the tapered housing. A tapered plunger is moveable within the tapered housing, the tapered plunger including a first polarity magnet at a first end closest to the first polarity magnet in the tapered housing and a second polarity magnet at a second end closest to the second polarity magnet in the tapered housing. Blood flowing into the tapered housing causes the tapered plunger to move and magnetic forces cause the tapered plunger to move back.

Alternatively or additionally, the magnetically actuated device may include an insert adapted to fit within the LAA, the insert including a magnetically polarized sleeve including first polarity magnets, and a plunger adapted to fit within the insert. The plunger includes an elongate body including one or more first polarity magnets disposed within the elongate body and a stopper disposed relative to a proximal end of the plunger. Blood entering the insert pushes on the stopper, and magnetic forces cause the plunger to move back.

Alternatively or additionally, the magnetically actuated device may include an annular structure having a first magnetic polarity along an inner surface of the annular structure and a second magnetic polarity along an outer surface of the annular structure, and a magnetically actuatable component secured relative to the annular structure, the magnetically actuatable component having an outer surface having the first magnetic polarity such that magnetic repulsion between the annular structure and the magnetically actuatable component causes movement of the magnetically actuated component.

Alternatively or additionally, the magnetically actuated device may include one or more tethers securing the magnetically actuatable component relative to the annular structure.

Alternatively or additionally, the annular structure may include a ring adapted to span across the LAA.

Alternatively or additionally, the annular structure may include an elongate cylinder.

Another example may be found in a magnetically actuated device for reducing blood stagnation within a left atrial appendage (LAA). The magnetically actuated device includes an annular structure and a magnetically actuatable component secured relative to the annular structure. The annular structure includes an inner segment defining an inner surface of the annular structure, the inner segment having a first magnetic polarity, and an outer segment defining an outer surface of the annular structure, the outer segment having a second magnetic polarity. The magnetically actuatable component includes an outer surface having the first magnetic polarity such that magnetic repulsion between the annular structure and the magnetically actuatable component causes movement of the magnetically actuated component.

Alternatively or additionally, the magnetically actuated device may further include one or more tethers securing the magnetically actuatable component relative to the annular structure.

Alternatively or additionally, at least some of the one or more tethers may be elastic.

Alternatively or additionally, the annular structure may be adapted to be suspended within the LAA via one or more anchoring tethers extending from the annular structure to a side wall of the LAA.

Alternatively or additionally, the annular structure may be adapted to be secured directly to a side wall of the LAA.

Alternatively or additionally, the annular structure may include a plurality of magnets each having a first polarity end and a second polarity end, and each of the plurality of magnets are arranged such that the first polarity end of each magnet forms the inner segment of the annular structure and the second polarity end of each magnet forms the outer segment of the annular structure.

Alternatively or additionally, the magnetically actuatable component may include an elongate magnet with one end having a first polarity and a second end having a second polarity, and wherein the second end is secured within the LAA and the first end is tethered relative to the annular structure.

Alternatively or additionally, the annular structure may include a first ring having an inner surface having a first polarity and an outer surface having a second polarity and a second ring axially spaced from the first ring, the second ring having an outer surface having a first polarity and an inner surface having a second polarity. The magnetically actuated component may include an elongate magnet suspended between the first ring and the second ring, with a first polarity end of the elongate magnet disposed closest to the first ring and a second polarity end of the elongate magnet disposed closest to the second ring.

Another example may be found in a magnetically actuated device for reducing blood stagnation within a left atrial appendage (LAA). The magnetically actuated device includes an elongate cylindrical structure having an inner segment defining an inner surface of the elongate cylindrical structure, the inner segment having a first magnetic polarity, and an outer segment defining an outer surface of the elongate cylindrical structure, the outer segment having a second magnetic polarity. A magnetically actuatable component is secured relative to the elongate cylindrical structure via one or more elastic tethers, the magnetically actuatable component having an outer surface having the first magnetic polarity such that magnetic repulsion between the elongate cylindrical structure and the magnetically actuatable component causes movement of the magnetically actuated component.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
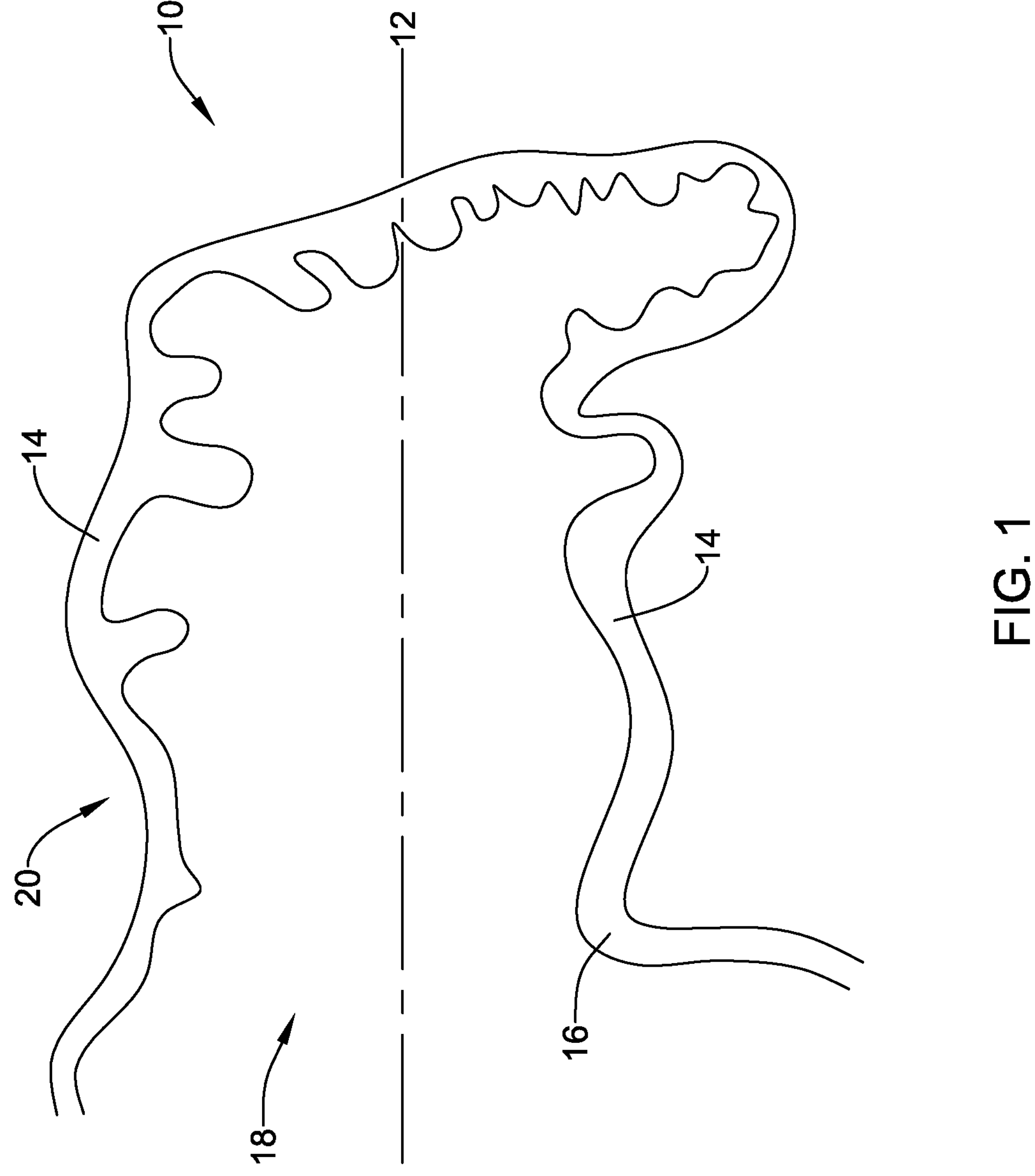
FIG. 1 is a partial cross-sectional view of an LAA (left atrial appendage)

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the present disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the present disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following figures illustrate selected components and/or arrangements of an implant for occluding the left atrial appendage, a system for occluding the left atrial appendage, and/or methods of using the implant and/or the system. It should be noted that in any given figure, some features may not be shown, or may be shown schematically, for simplicity. Additional details regarding some of the components of the implant and/or the system may be illustrated in other figures in greater detail. While discussed in the context of occluding the left atrial appendage, the implant and/or the system may also be used for other interventions and/or percutaneous medical procedures within a patient. Similarly, the devices and methods described herein with respect to percutaneous deployment may be used in other types of surgical procedures, as appropriate. For example, in some examples, the devices may be used in a non-percutaneous procedure. Devices and methods in accordance with the disclosure may also be adapted and configured for other uses within the anatomy.

FIG. 1 is a partial cross-sectional view of a left atrial appendage 10. In some embodiments, the left atrial appendage (LAA) 10 may have a complex geometry and/or irregular surface area. It will be appreciated that the illustrated LAA 10 is merely one of many possible shapes and sizes for the LAA 10, which may vary from patient to patient. Those of skill in the art will also recognize that the medical devices, systems, and/or methods disclosed herein may be adapted for various sizes and shapes of the LAA 10, as necessary. The left atrial appendage 10 may include a generally longitudinal axis 12 arranged along a depth of a main body 20 of the left atrial appendage 10. The main body 20 may include a lateral wall 14 and an ostium 16 forming a proximal mouth 18. In some examples, a lateral extent of the ostium 16 and/or the lateral wall 14 may be smaller or less than a depth of the main body 20 along the longitudinal axis 12, or a depth of the main body 20 may be greater than a lateral extent of the ostium 16 and/or the lateral wall 14. In some examples, the LAA 10 may narrow quickly along the depth of the main body 20 or the left atrial appendage may maintain a generally constant lateral extent along a majority of depth of the main body 20. In some examples, the LAA 10 may include a distalmost region formed or arranged as a tail-like element associated with a distal portion of the main body 20. In some examples, the distalmost region may protrude radially or laterally away from the longitudinal axis 12.

In some cases, and particularly during times of atrial fibrillation, blood flow within the LAA 10 may become stagnant. Stagnant blood flow within the LAA 10 may lead to blood clots, which can lead to stroke. In some cases, creating blood flow within the LAA 10 may help to reduce stagnation and thus reduce the likelihood of blood clot formation, especially during atrial fibrillation. FIGS. 2 through 14 provide examples of magnetically actuatable devices that may be implanted within the LAA 10 in order to reduce stagnation. In some cases, these magnetically actuatable devices may operate at all times.

In some cases, a method for reducing blood stagnation within the LAA 10 may include using a magnetic field to cause motion within the LAA 10. As an example, a magnetically actuated device may be implanted within the LAA 10. The magnetically actuated device may be caused to become actuated, which causes the magnetically actuated device to cause motion within the LAA 10. In some cases, causing the magnetically actuated device to become actuated may include applying an external magnetic field to the magnetically actuated device by creating an external magnetic field from outside of the patient's body.

Figure 2:
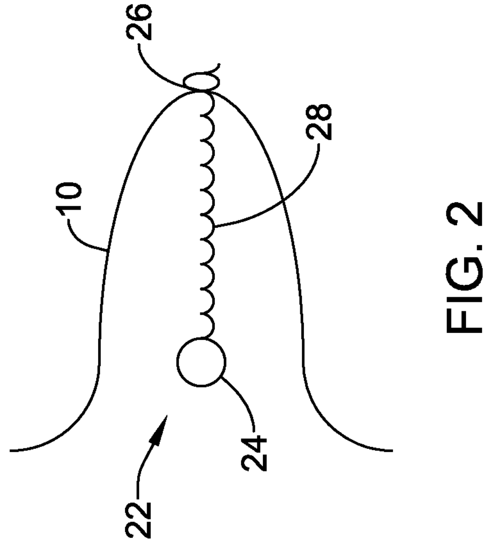
FIG. 2 is a schematic view of an illustrative magnetically actuated actuatable device.

FIG. 2 is a schematic view of an illustrative magnetically actuated device 22 that is adapted to be actuated via an external magnetic field. The magnetically actuated device 22 includes a magnetically actuated component 24, an anchor 26 that is adapted to anchor the magnetically actuated device 22 to an interior of the LAA 10, and a tether 28 that extends between the magnetically actuated component 24 and the anchor 26. In some cases, the magnetically actuated component 24 may be made of a material that is responsive to a magnetic field. Examples of such materials include ferrous materials such as steel. In some cases, the magnetically actuated component 24 may include a magnet such as a permanent magnet. In some cases, the magnetically actuated component 24 may include a ferrous material such as 440 stainless steel or other steel materials. Other materials are also contemplated. The tether 28 may be an elastic cord. The tether 28 may be a stiff cord. In some cases, the tether 28 may be a spring. The tether 28 may be adapted to allow the magnetically actuated component 24 to move in response to an applied magnetic field.

Figure 3:
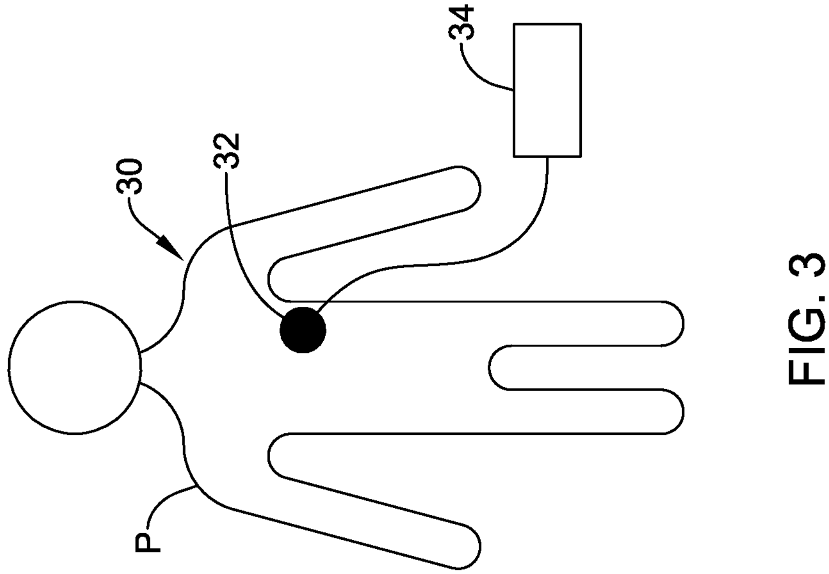
FIG. 3 is a schematic view of an illustrative apparatus for magnetically actuating the magnetically actuatable device of FIG. 2.

FIG. 3 is a schematic view of an illustrative apparatus 30 for applying a magnetic field, shown disposed relative to a person P. The apparatus 30 includes a magnet 32 and a power source 34. The magnet 32 may be an electromagnet, for example, and may be adapted to switch its polarity back and forth to help cause movement of the magnetically actuated component 24. In some cases, the magnet 32 may be a permanent magnet. The power supply 34 may include a battery, for example. In some cases, the power supply 34 may be adapted to be plugged into an outlet for electrical power. In some cases, the person P may utilize the apparatus 30 when they believe that they are in atrial fibrillation, such as when a separate sensor (not shown) informs them that they are in atrial fibrillation.

Figure 4:
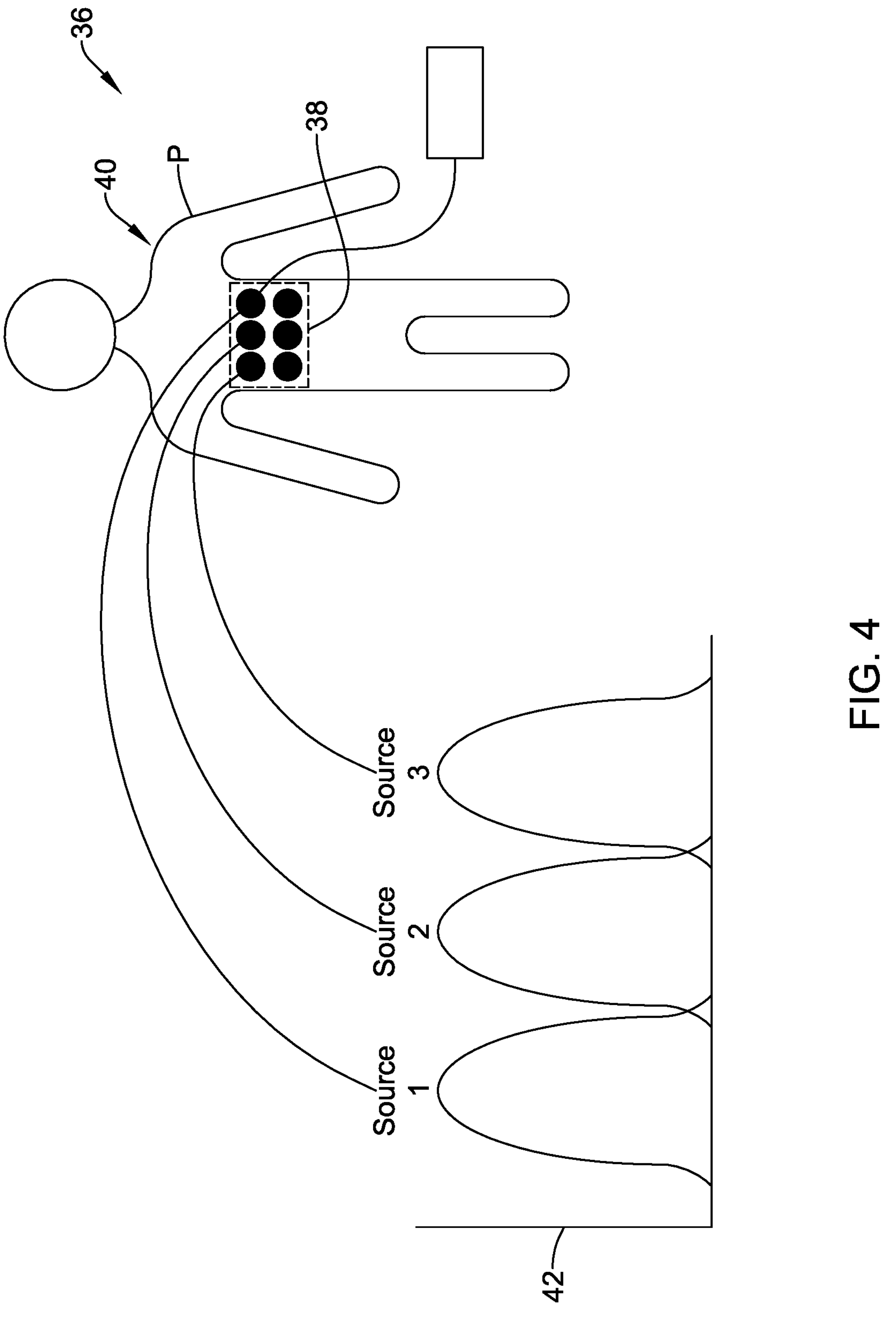
FIG. 4 is a schematic view of an illustrative apparatus for magnetically actuating the magnetically actuatable device of FIG. 2.

FIG. 4 is a schematic view of an illustrative apparatus 36 that may be used for generating a magnetic field, shown disposed relative to the person P. In some cases, the apparatus 36 may include a vest 38 that the person P wears, with a number of magnets 40 disposed on the vest 38. The magnets 40 may be electromagnets that can be actuated asynchronously in order to create motion of the magnetically actuated component 24. The magnets 40 may be considered as creating an external magnetic field. By using multiple magnets 40, the magnetically actuated component 24 may be pulled in multiple directions, thereby increasing movement. A graph 42 illustrates the use of multiple sources.

Figure 5:
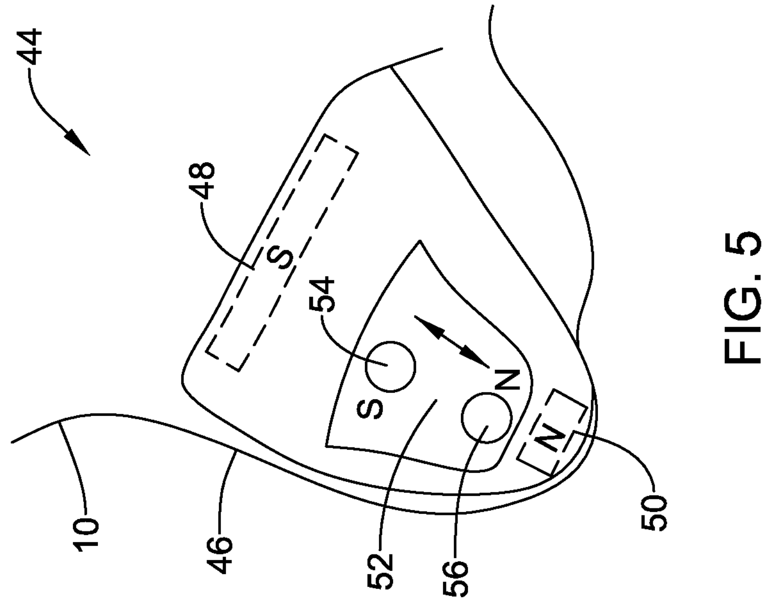
FIG. 5 is a schematic view of an illustrative magnetically actuated actuatable device.
Figure 8:
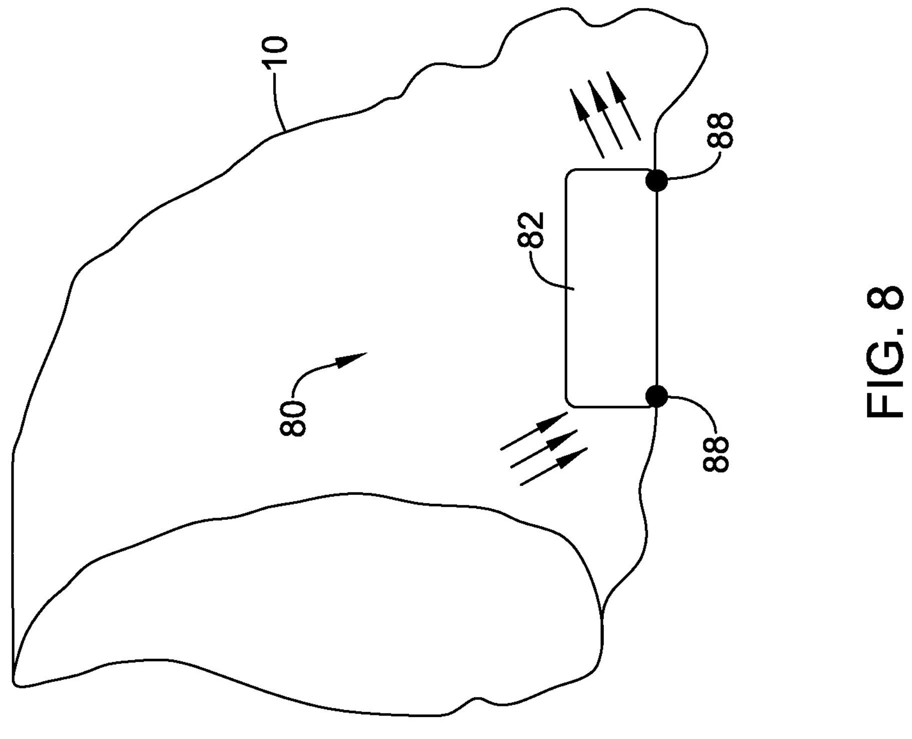
FIG. 8 is a schematic view of an illustrative magnetically actuated actuatable device shown disposed in an LAA.

In some cases, causing the magnetically actuated device to become actuated may include subjecting the magnetically actuated device to blood flow within the LAA 10. FIG. 5 is a schematic view of an illustrative magnetically actuated device 44. The magnetically actuated device 44 includes a tapered housing 46 that is adapted to fit within the LAA 10 and to allow blood flow within the tapered housing 46. As shown, the tapered housing 46 includes a south pole magnet 48 located at a proximal end of the tapered housing 46 and a north pole magnet 50 located at a distal end of the tapered housing 46. A tapered plunger 52 includes a south pole magnet 54 at a first end closest to the south pole magnet 48 and a north pole magnet 56 at a second end closest to the north pole magnet 50. It will be appreciated that blood flowing into the tapered housing 46 may cause movement of the tapered plunger 52 while magnetic forces will cause the tapered plunger 52 to move back. As the tapered plunger 52 moves upward (in the illustrated orientation), the south pole magnet 48 and the south pole magnet 54 will create a repellant force that pushes the tapered plunger 52 away from the south pole magnet 48. As the tapered plunger 52 moves downward, the north pole magnet 50 and the north pole magnet 56 will create a repellant force that pushes the tapered plunger 52 away from the north pole magnet 56. Movement of the tapered plunger 52 as a result of repulsive magnetic forces, as well as blood flow, will cause further movement of blood near the tapered plunger 52. In some instances, this blood movement may be sufficient to create eddies within the LAA that are enough to prevent or at least reduce stagnation within the LAA 10. By reducing stagnation, the risk of clot development may be reduced.

While the magnetically actuated device 44 shows particular magnets as being south pole magnets and other magnets as being north pole magnets, this is merely illustrative. In some cases, the magnet 48 and the magnet 54 may each be a first polarity and the magnet 50 and the magnet 56 may each be a second polarity. In some cases, it doesn't matter which pairing of magnets are both north pole magnets and which pairing of magnets are both south pole magnets as long as they are in opposition. In some cases, all four magnets may be north pole magnets. IN some cases, all four magnets may be south pole magnets. In some cases, referring to a magnet as a north pole magnet or a south pole magnet actually means that the referenced polarity is closest to a particular location, as all magnets have a north pole end and a south pole end. Magnets may be considered as referring to permanent magnets, particularly if not modified by the prefix "electro".

Figure 6:
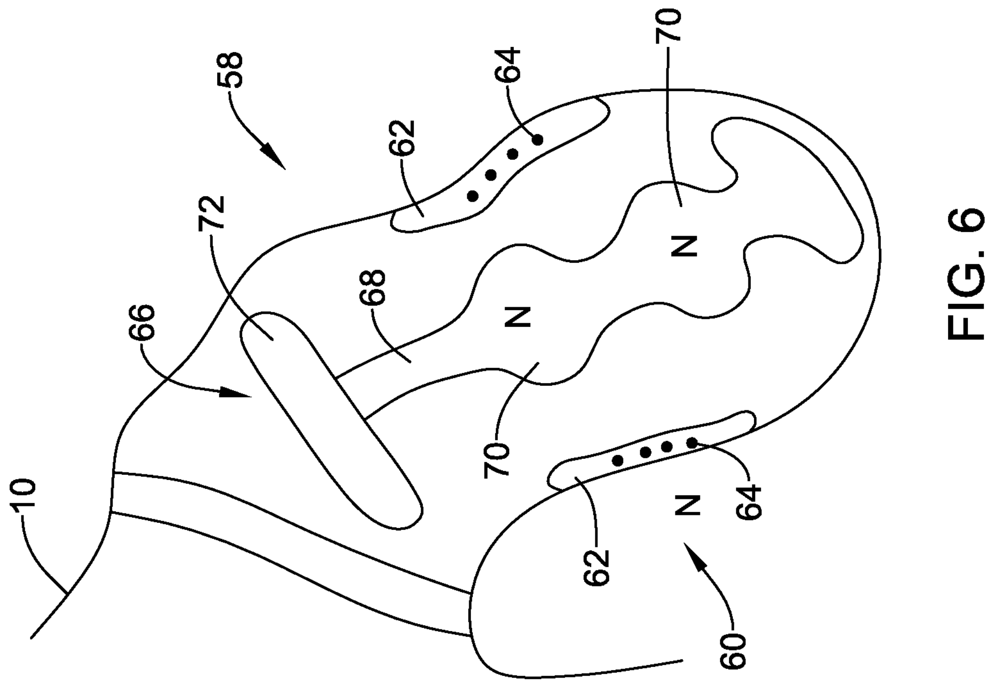
FIG. 6 is a schematic view of an illustrative magnetically actuated actuatable device.

FIG. 6 is a schematic view of an illustrative magnetically actuated device 58 disposed within the LAA 10. The magnetically actuated device 58 includes an insert 60 that is adapted to fit within the LAA 10. The insert 60 includes a magnetically polarized sleeve 62 that includes a number of first polarity magnets 64. A plunger 66 is adapted to fit within the insert 60. The plunger 66 includes an elongate body 68 that includes one or more first polarity magnets 70. While the magnets 64 and the magnets 70 are shown as being north pole magnets, this is not required. In some cases, the magnets 64 and the magnets 70 may both be south pole magnets, for example. The plunger 66 includes a stopper 72 that is disposed relative to a proximal end of the plunger 66. Blood entering the insert 60 pushes on the stopper 72, causing the plunger 66 to move in a first direction, and magnetic forces between the magnets 64 and the magnets 70 cause the plunger 66 to move back. As the plunger 66 moves, this will cause corresponding movement in the blood around the plunger 66. In some instances, this blood movement may be sufficient to create eddies within the LAA that are enough to prevent or at least reduce stagnation within the LAA 10. By reducing stagnation, the risk of clot development may be reduced.

Figure 7:
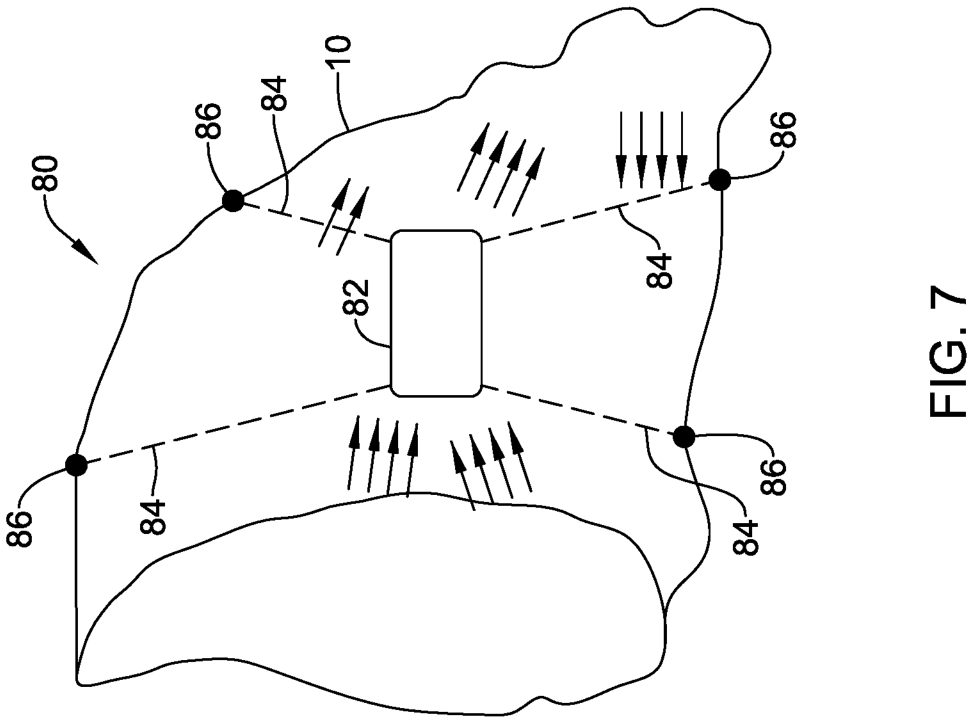
FIG. 7 is a schematic view of an illustrative magnetically actuated actuatable device shown disposed in an LAA.

FIG. 7 is a schematic view of an illustrative magnetically actuated device 80 disposed within the LAA 10. The magnetically actuated device 80 includes a cylinder 82 that is positioned within the LAA 10. The cylinder may be considered as being an annular structure. In some cases, as shown, the magnetically actuated device 80 may include several tethers 84 that each extend from the cylinder 82 to an anchor 86 that is adapted to be secured to tissue within the LAA 10. The tethers 84 may be elastic or inelastic, for example, and may be formed of any suitable material. The anchors 86 may be adapted to extend partially into the side wall of the LAA 10 in order to anchor the cylinder 82 in position. In some cases, as seen for example in FIG. 8, the magnetically actuated device 80 includes the cylinder 82, but may instead position the cylinder 82 along a side wall of the LAA 10. In this case, the cylinder 82 may include anchors 88 that are adapted to extend partially into the side wall of the LAA 10 in order to anchor the cylinder 82 in position.

In some cases, the magnetically actuated device 80, and the other magnetically actuated devices described herein, may be tuned to have a particular resonant frequency that corresponds more closely to a natural frequency that occurs during atrial fibrillation. The magnetically actuated device 80, and the other magnetically actuated devices described herein, will still function at other frequencies, but may work even better at that resonant frequency. As a result, the magnetically actuated device 80, and the other magnetically actuated devices described herein, may be even more effective during atrial fibrillation. In some cases, atrial fibrillation may result in a heart rate that is between 228 to 480 beats per minute.

Figure 9:
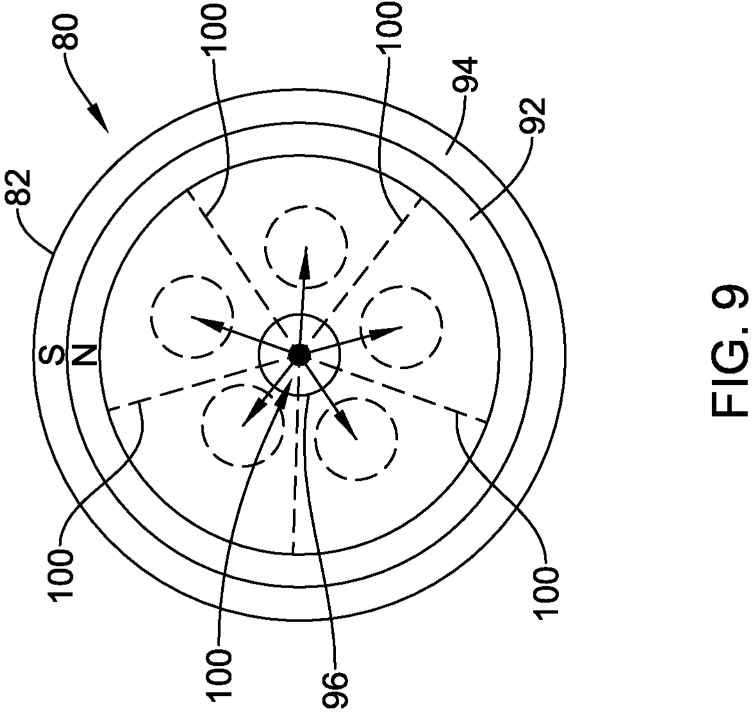
FIG. 9 is a schematic end view of the illustrative magnetically actuated actuatable device of FIG. 7.

FIG. 9 is an end view of the magnetically actuated device 80. As seen, the cylinder 82 may be considered as including an inner segment 92 and an outer segment 94. In some cases, the inner segment 92 and the outer segment 94 may each be monolithic structures. In some cases, the inner segment 92 and the outer segment 94 may be formed from a plurality of magnets, with each magnet having a north pole and a south pole. Each magnet may be arranged such that the inner segment 92 corresponds to a first polarity of each of the magnets and the outer segment 94 corresponds to a second polarity of each of the plurality of magnets. As shown, the inner segment 92 is labeled as south pole and the outer segment 94 is labeled as north pole. It will be appreciated that this may easily be reversed.

The magnetically actuated device 80 includes a magnetically actuated component 96. In some instances, the magnetically actuated component 96 may be suspended within an interior of the cylinder 82 via a tether 98 that extends upward to an apex 102 formed between a number of struts 100, with the struts secured relative to the cylinder 82. The tether 98 helps to locate the magnetically actuated component 96 within the cylinder 82, and prevents the magnetically actuated component 96 from exiting the cylinder 82. Magnetic forces between magnets disposed within the magnetically actuated component 96 and those forming or otherwise in the inner segment 92 may cause the magnetically actuated component 96 to move into the positions shown in dashed line. This may occur when the outermost magnetic pole of the magnets within the magnetically actuated component 96 match the polarity of the inner segment 92.

Figure 10:
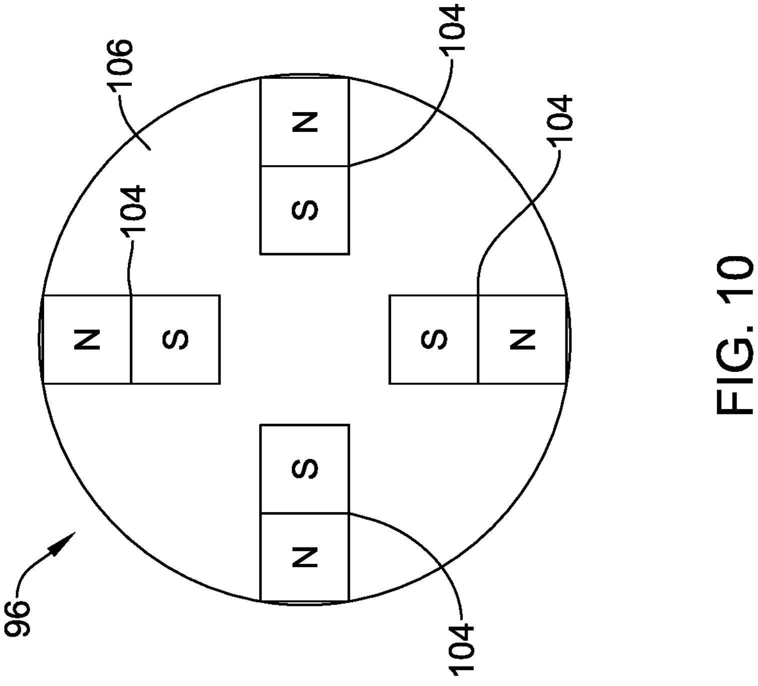
FIG. 10 is a schematic view of a portion of the illustrative magnetically actuated actuatable device of FIG. 7.

FIG. 10 is a schematic view of the magnetically actuated component 96. In some instances, the magnetically actuated component 96 may include a number of magnets 104 that are disposed within a polymeric ball 106. As shown, each of the magnets 104 has its north pole facing outward such that the north pole of each of the magnets 104 will interact with the corresponding north pole facing of the inner segment 92. This causes a repulsive force that will cause the magnetically actuated component 96 to keep moving. While the magnetically actuated component 96 may theoretically reach an equilibrium point between the repulsive magnetic forces, in practice cardiac movement during the cardiac cycle will likely keep the magnetically actuated component 96 from reaching its theoretical equilibrium point. In some cases, each of the magnets 104 may be placed within the magnetically actuated component 96 with its south pole facing outward as long as the magnets forming the cylinder 82 are similarly placed such that the inner segment 92 has a south pole.

As the magnetically actuated component 96 moves, this will cause corresponding movement in the blood around the magnetically actuated component 96. In some instances, this blood movement may be sufficient to create eddies within the LAA that are enough to prevent or at least reduce stagnation within the LAA 10. By reducing stagnation, the risk of clot development may be reduced.

Figure 11:
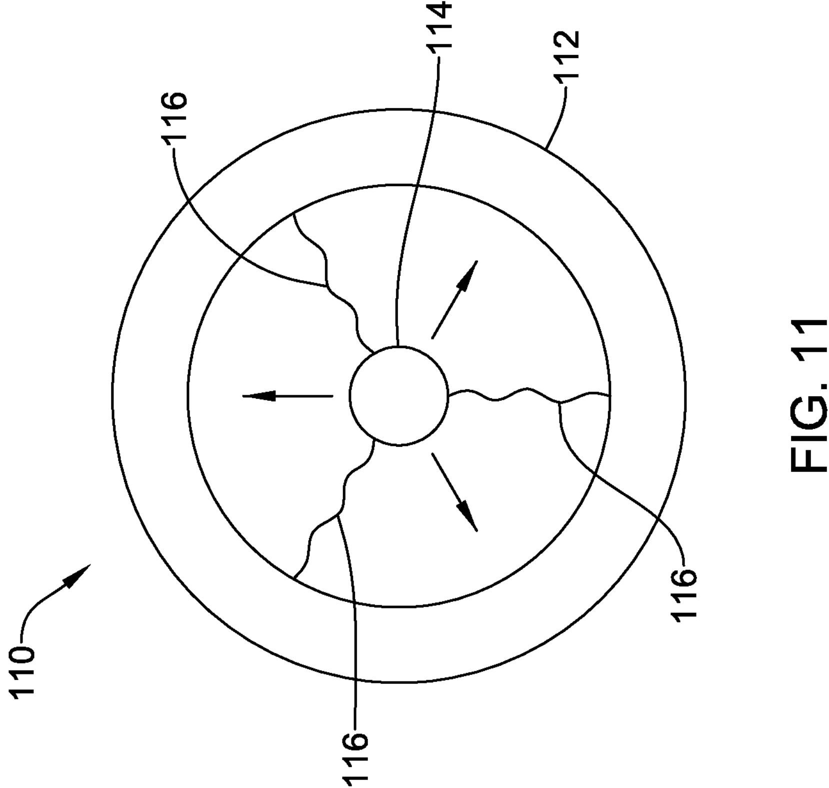
FIG. 11 is a schematic view of an illustrative magnetically actuated actuatable device.

FIG. 11 is a schematic view of a magnetically actuated actuatable device 110 that may be disposed within the LAA 10. The magnetically actuatable device 110 includes an outer ring 112 that may be sized to span the LAA 10. The outer ring 112 may be considered as being an annular structure. In some cases, the outer ring 112 may be smaller than the LAA 10, in which case the outer ring 112 may be secured relative to the LAA 10 using one or more tethers and anchors (not shown). The magnetically actuatable device 110 includes a magnetically actuatable component 114 that is held captive within the outer ring 112 via several tethers 116. It will be appreciated that in some instances, each of the tethers 116 may be elastic.

The outer ring 112 is magnetic, and may include a plurality of magnets each arranged with a first polarity facing inward and a second polarity facing outward. Similarly, the magnetically actuated component 114 may include several magnets arranged with a first polarity facing outward and a second polarity facing inward. The resulting repulsive forces between the first polarity of the outer ring 112 and the same first polarity of the magnets within the magnetically actuated component 114 will cause the magnetically actuated component 114 to move relative to the outer ring 112.

As the magnetically actuated component 114 moves, this will cause corresponding movement in the blood around the magnetically actuated component 114. In some instances, this blood movement may be sufficient to create eddies within the LAA that are enough to prevent or at least reduce stagnation within the LAA 10. By reducing stagnation, the risk of clot development may be reduced.

Figure 12:
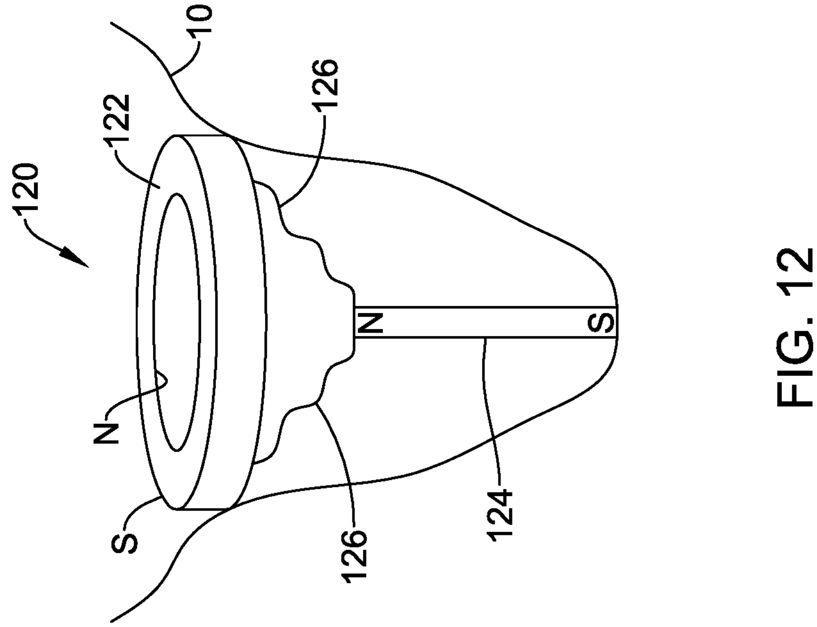
FIG. 12 is a schematic view of an illustrative magnetically actuated actuatable device shown disposed in an LAA.

FIG. 12 is a schematic view of an illustrative magnetically actuated actuatable device 120 shown disposed within the LAA 10. The illustrative magnetically actuated actuatable device 120 includes an outer ring 122 that has, as shown, a north polarity on an inner surface of the outer ring 122 and a south polarity on an outer surface of the outer ring 122. It will be appreciated that the outer ring 122 may include a number of magnets, each with its north pole facing inward and its south pole facing outward. The magnetically actuated actuatable device 120 includes an elongate magnet 124 having a north pole at an upper (in the illustrated orientation) end and a south pole at a lower end of the elongate magnet 124. The lower end of the elongate magnet 124 may be attached to the LAA 10. The upper end of the elongate magnet 124 may be attached to the outer ring 122 via tethers 126. The tethers 126 may be elastic.

Magnetic forces between the outer ring 122 and the elongate magnet 124 will cause the north pole end of the elongate magnet 124 to move around. As the elongate magnet 124 moves, this will cause corresponding movement in the blood around the elongate magnet 124. In some instances, this blood movement may be sufficient to create eddies within the LAA that are enough to prevent or at least reduce stagnation within the LAA 10. By reducing stagnation, the risk of clot development may be reduced. It will be appreciated that the relative polarity of the inner and outer surfaces of the outer ring 122 and those of the elongate magnet 124 may be reversed from what is shown, and the magnetically actuated actuatable device 120 will work just as well.

Figure 13:
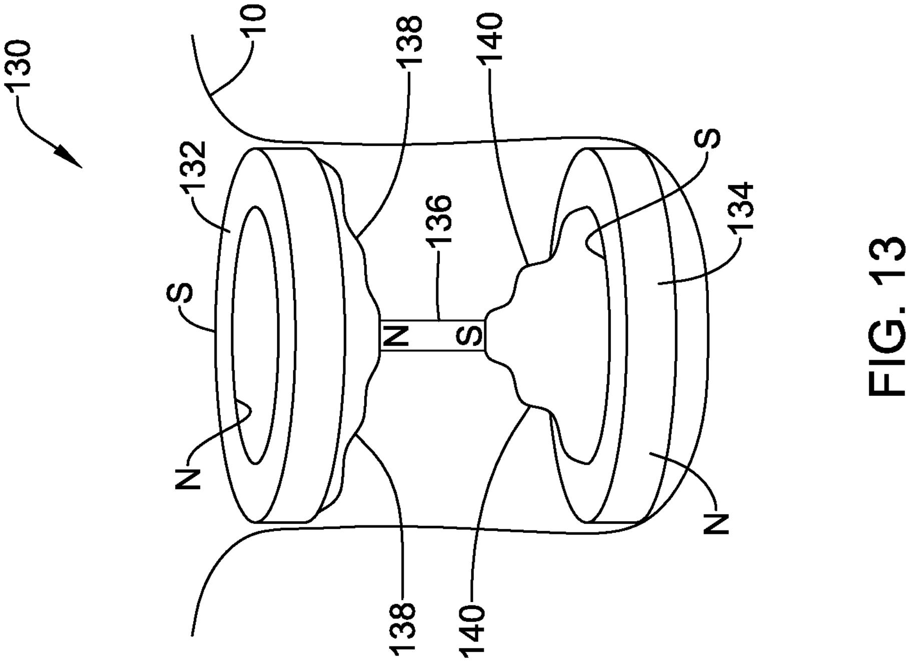
FIG. 13 is a schematic view of an illustrative magnetically actuated actuatable device shown disposed in an LAA.

FIG. 13 is a schematic view of an illustrative magnetically actuated actuatable device 130 shown disposed within the LAA 10. The illustrative magnetically actuated actuatable device 130 includes an upper (in the illustrated orientation) ring 132 that has, as shown, a north polarity on an inner surface of the upper ring 132 and a south polarity on an outer surface of the upper ring 132. It will be appreciated that the upper ring 132 may include a number of magnets, each with its north pole facing inward and its south pole facing outward. The magnetically actuated actuatable device 130 includes a lower (in the illustrated orientation) ring 134 that has, as shown, a south polarity on an inner surface of the lower ring 134 and a north polarity on an outer surface of the lower ring 134. It will be appreciated that the lower ring 134 may include a number of magnets, each with its north pole facing inward and its south pole facing outward.

The magnetically actuated actuatable device 130 includes an elongate magnet 136 having a north pole at an upper (in the illustrated orientation) end and a south pole at a lower end of the elongate magnet 136. The elongate magnet 136 is held in place via tethers 138 that extend between the elongate magnet 136 and the upper ring 132 as well as tethers 140 that extend between the elongate magnet 136 and the lower ring 134. The tethers 138 and 140 may be elastic.

Magnetic forces between the upper ring 132 and the north pole end of the elongate magnet 136 and magnetic forces between the lower ring 134 and the south pole end of the elongate magnet 136 will cause movement of the elongate magnet 136. As the elongate magnet 136 moves, this will cause corresponding movement in the blood around the elongate magnet 136. In some instances, this blood movement may be sufficient to create eddies within the LAA that are enough to prevent or at least reduce stagnation within the LAA 10. By reducing stagnation, the risk of clot development may be reduced. It will be appreciated that the relative polarity of the inner and outer surfaces of the upper ring 132, the lower ring 134 and those of the elongate magnet 136 may be reversed from what is shown, and the magnetically actuated actuatable device 130 will work just as well.

Figure 14:
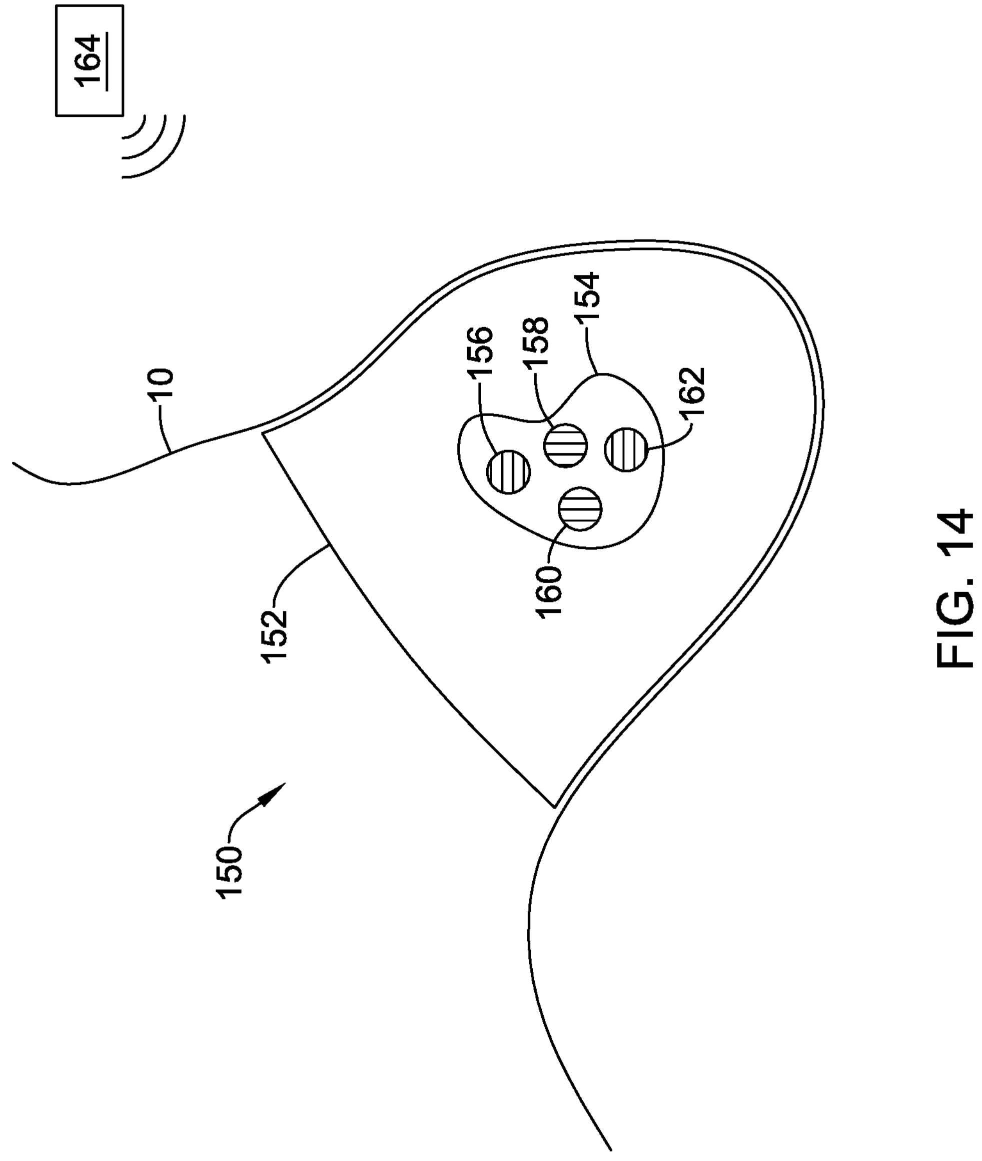
FIG. 14 is a schematic view of an illustrative magnetically actuated actuatable device shown disposed in an LAA.

FIG. 14 is a schematic view of an illustrative magnetically actuated actuatable device 150 shown disposed within the LAA 10. In some instances, the magnetically actuated actuatable device 150 may be adapted to respond to an externally applied magnetic field. In some instances, the externally applied magnetic field may be an alternating magnetic field in which the polarity of the magnetic field keeps alternating. As an example, the magnet 32 (FIG. 3) or the magnets 40 (FIG. 4) may be used as a source of an externally applied magnetic field. These magnets may be electromagnets, and may be adapted to generate an alternating magnetic field.

The illustrative magnetically actuated actuatable device 150 includes a structure 152 that is adapted to fit within the LAA 10. While shown schematically, in some instances the structure 152 may be a braided or woven structure that allows blow to flow in and out of an interior of the structure 152, but is adapted to constrain a magnetically actuated component 154. The magnetically actuated component 154 may include a number of polarizing beads disposed within an elastomeric membrane. As shown, a bead 156 and a bead 162 may each have a first polarity and a bead 158 and 160 may each have a second polarity that is opposite the first polarity. While a total of four beads are shown, this is merely illustrative, as the magnetically actuated component 154 may include any number of polarizing beads.

As an example, the bead 156 and the bead 162 may each include an outward-facing north pole and the beads 158 and 160 may each include an outward-facing south pole. Alternatively, bead 156 and the bead 162 may each include an outward-facing south pole and the beads 158 and 160 may each include an outward-facing north pole. In some instances, an externally applied magnetic field may cause the magnetically actuated component 154 to move within the structure 152 as the beads 156, 158, 160 and 162 react to the externally applied magnetic field. When the externally applied magnetic field is of the first polarity, the beads 156 and 162 may react to a repulsive force while the beads 158 and 160 may react to an attractive force.

When the externally applied magnetic field is of the second polarity, the beads 156 and 162 may react to an attractive force while the beads 158 and 160 may react to a repulsive force As the magnetically actuated component 154 moves, this will cause corresponding movement in the blood around the magnetically actuated component 154. In some instances, this blood movement may be sufficient to create eddies within the LAA that are enough to prevent or at least reduce stagnation within the LAA 10. By reducing stagnation, the risk of clot development may be reduced.

The materials that can be used for the devices described herein may include those commonly associated with medical devices. The devices described herein, or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super-elastic nitinol in that the linear elastic and/or non-super-elastic nitinol does not display a substantial "superelastic plateau" or "flag region" in its stress/strain curve like super-elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super-elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, the devices described herein, or components thereof, may also be doped with, made of, or otherwise include a radiopaque material. Radiopaque materials are understood to be materials capable of producing a relatively bright image on a fluoroscopy screen or another imaging technique during a medical procedure. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into the devices described herein, or components thereof. For example, the devices described herein, or components thereof, may be made of a material that does not substantially distort the image and create substantial artifacts (e.g., gaps in the image). Certain ferromagnetic materials, for example, may not be suitable because they may create artifacts in an MRI image. The devices described herein, or components thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of the devices described herein in order to define a generally smooth outer surface. In other embodiments, however, such a sheath or covering may be absent. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the devices described herein may be sandblasted, beadblasted, sodium bicarbonate-blasted, electropolished, etc. In these as well as in some other embodiments, a coating, for example a lubricious, a hydrophilic, a protective, or other type of coating may be applied. Alternatively, a sheath may include a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

Portions of the devices described herein may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present disclosure.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method for reducing blood stagnation within a left atrial appendage (LAA) using a magnetic field to cause motion within the LAA, the method comprising:
- implanting a magnetically actuated device within the LAA;
- causing the magnetically actuated device to become actuated, the magnetically actuated device causing motion within the LAA.

2. The method of claim 1, wherein causing the magnetically actuated device to become actuated comprises applying an external magnetic field to the magnetically actuated device.

3. The method of claim 2, wherein the magnetically actuated device comprises:
- a magnetically actuated component;
- an anchor adapted to anchor the magnetically actuated component to an interior of the LAA; and
- a flexible tether extending between the magnetically actuated component and the anchor.

4. The method of claim 3, wherein the magnetically actuated component comprises a magnet or a magnetic material.

5. The method of claim 1, wherein causing the magnetically actuated device to become actuated comprises subjecting the magnetically actuated device to blood flow within the LAA.

6. The method of claim 5, wherein the magnetically actuated device comprises:
- a tapered housing adapted to fit within the LAA and to allow blood flow within the tapered housing, the tapered housing comprising:
  - a first polarity magnet disposed within a proximal end of the tapered housing; and
  - a second polarity magnet disposed within a distal end of the tapered housing;
- a tapered plunger moveable within the tapered housing, the tapered plunger including a first polarity magnet at a first end closest to the first polarity magnet in the tapered housing and a second polarity magnet at a second end closest to the second polarity magnet in the tapered housing;
- wherein blood flowing into the tapered housing causes the tapered plunger to move and magnetic forces cause the tapered plunger to move back.

7. The method of claim 5, wherein the magnetically actuated device comprises:
- an insert adapted to fit within the LAA, the insert including a magnetically polarized sleeve including first polarity magnets;
- a plunger adapted to fit within the insert, the plunger comprising:
  - an elongate body including one or more first polarity magnets disposed within the elongate body; and
  - a stopper disposed relative to a proximal end of the plunger;
- wherein blood entering the insert pushes on the stopper, and magnetic forces cause the plunger to move back.

8. The method of claim 5, wherein the magnetically actuated device comprises:
- an annular structure having a first magnetic polarity along an inner surface of the annular structure and a second magnetic polarity along an outer surface of the annular structure;
- a magnetically actuatable component secured relative to the annular structure, the magnetically actuatable component having an outer surface having the first magnetic polarity such that magnetic repulsion between the annular structure and the magnetically actuatable component causes movement of the magnetically actuated component.

9. The method of claim 8, wherein the magnetically actuated device comprises one or more tethers securing the magnetically actuatable component relative to the annular structure.

10. The method of claim 8, wherein the annular structure comprises a ring adapted to span across the LAA.

11. The method of claim 8, wherein the annular structure comprises an elongate cylinder.

12. A magnetically actuated device for reducing blood stagnation within a left atrial appendage (LAA), the magnetically actuated device comprising:
- an annular structure comprising:
  - an inner segment defining an inner surface of the annular structure, the inner segment having a first magnetic polarity;
  - an outer segment defining an outer surface of the annular structure, the outer segment having a second magnetic polarity; and
- a magnetically actuatable component secured relative to the annular structure, the magnetically actuatable component having an outer surface having the first magnetic polarity such that magnetic repulsion between the annular structure and the magnetically actuatable component causes movement of the magnetically actuated component.

13. The magnetically actuated device of claim 12, further comprising one or more tethers securing the magnetically actuatable component relative to the annular structure.

14. The magnetically actuated device of claim 13, wherein at least some of the one or more tethers are elastic.

15. The magnetically actuated device of claim 12, wherein the annular structure is adapted to be suspended within the LAA via one or more anchoring tethers extending from the annular structure to a side wall of the LAA.

16. The magnetically actuated device of claim 12, wherein the annular structure is adapted to be secured directly to a side wall of the LAA.

17. The magnetically actuated device of claim 12, wherein the annular structure comprises a plurality of magnets each having a first polarity end and a second polarity end, and each of the plurality of magnets are arranged such that the first polarity end of each magnet forms the inner segment of the annular structure and the second polarity end of each magnet forms the outer segment of the annular structure.

18. The magnetically actuated device of claim 12, wherein the magnetically actuatable component comprises an elongate magnet with one end having a first polarity and a second end having a second polarity, and wherein the second end is secured within the LAA and the first end is tethered relative to the annular structure.

19. The magnetically actuated device of claim 12, wherein:

the annular structure comprises:

a first ring having an inner surface having a first polarity and an outer surface having a second polarity; and a second ring axially spaced from the first ring, the second ring having an outer surface having a first polarity and an inner surface having a second polarity; and the magnetically actuated component comprises an elongate magnet suspended between the first ring and the second ring, with a first polarity end of the elongate magnet disposed closest to the first ring and a second polarity end of the elongate magnet disposed closest to the second ring.

20. A magnetically actuated device for reducing blood stagnation within a left atrial appendage (LAA), the magnetically actuated device comprising:

an elongate cylindrical structure comprising:

an inner segment defining an inner surface of the elongate cylindrical structure, the inner segment having a first magnetic polarity;

an outer segment defining an outer surface of the elongate cylindrical structure, the outer segment having a second magnetic polarity; and a magnetically actuatable component secured relative to the elongate cylindrical structure via one or more elastic tethers, the magnetically actuatable component having an outer surface having the first magnetic polarity such that magnetic repulsion between the elongate cylindrical structure and the magnetically actuatable component causes movement of the magnetically actuated component.

* * * * *